United States Patent [19]
Yamamoto et al.

[11] Patent Number: 5,946,208
[45] Date of Patent: Aug. 31, 1999

[54] POWER CONVERTER

[75] Inventors: Yasuhiro Yamamoto, Aichi; Yoshihiro Murai, Gifu, both of Japan

[73] Assignee: Kabushiki Kaisha Meidensha, Tokyo, Japan

[21] Appl. No.: 09/154,469

[22] Filed: Sep. 16, 1998

[51] Int. Cl.$^6$ .................................................. H02M 7/537
[52] U.S. Cl. .............................. 363/132; 363/41; 363/98
[58] Field of Search .................................. 363/16, 17, 40, 363/41, 97, 98, 131, 132

[56] References Cited

U.S. PATENT DOCUMENTS

| | | | |
|---|---|---|---|
| 4,333,134 | 6/1982 | Gurwicz | 363/17 |
| 5,303,140 | 4/1994 | Shimizu | 363/132 |

*Primary Examiner*—Peter S. Wong
*Assistant Examiner*—Y. J. Han
*Attorney, Agent, or Firm*—Foley & Lardner

[57] ABSTRACT

A PWM power converter includes a first switching branch of a first switching device and a first inductor between a positive source terminal and a load terminal and a second switching branch of a second inductor and a second switching device between the load terminal and a negative source terminal. To reduce noise and loss, the power converter is further provided with a series combination of third and fourth capacitors connected between the positive and negative source terminals, a series combination of first diode and first capacitor connected between a first junction point between the third and fourth capacitors and a second junction point between the first switching device and the first inductor, a series combination of second capacitor and second diode connected between a third junction point between the second inductor and the second switching device and a fourth junction point between the third and fourth capacitors, a series combination of third diode and third inductor connected between a fifth junction point between the first diode and the first capacitor and the positive source terminal, and a series combination of fourth inductor and fourth diode connected between the negative source terminal and a sixth junction point between the second capacitor and the second diode.

27 Claims, 21 Drawing Sheets

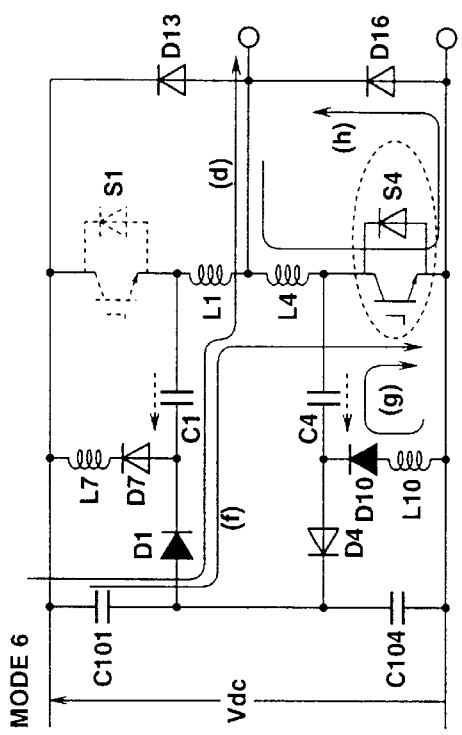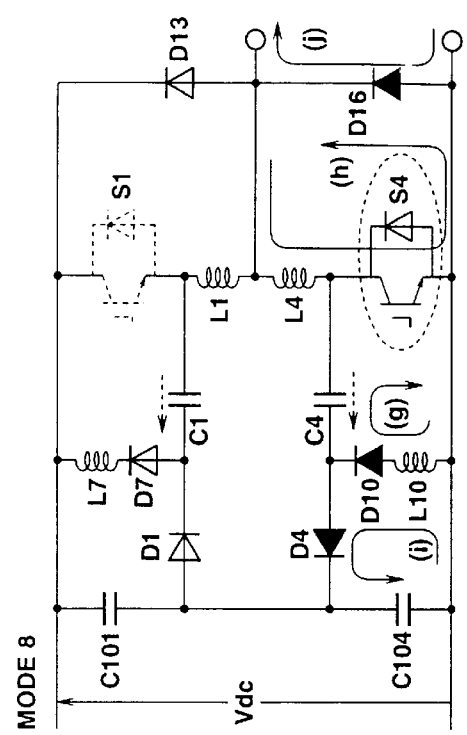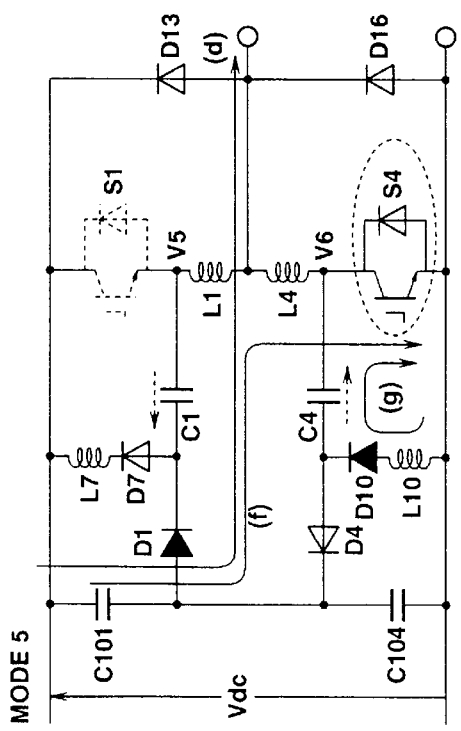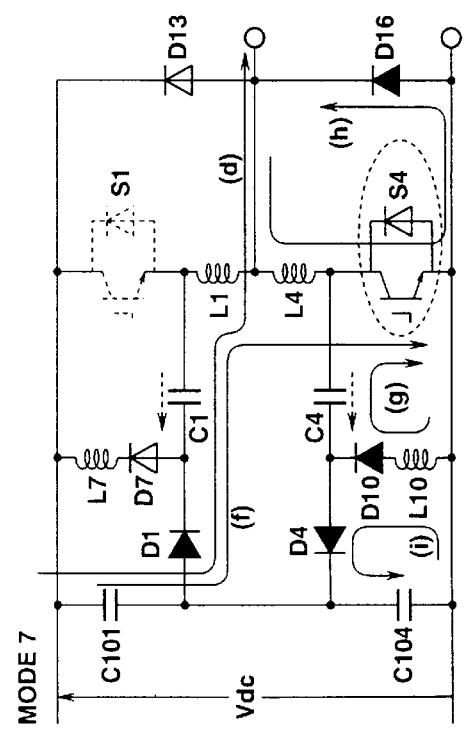

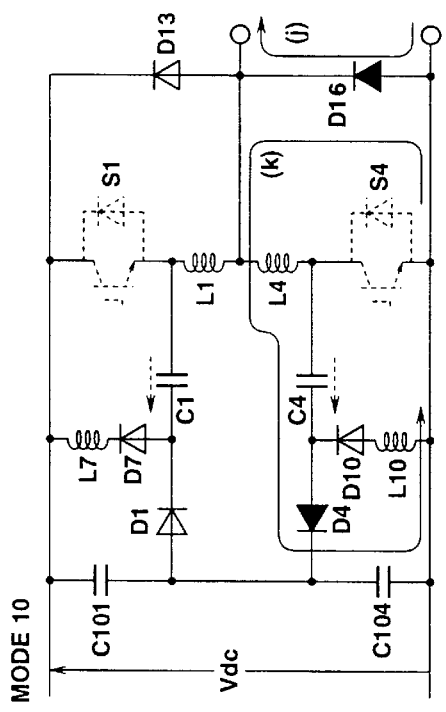
FIG.4B MODE 10
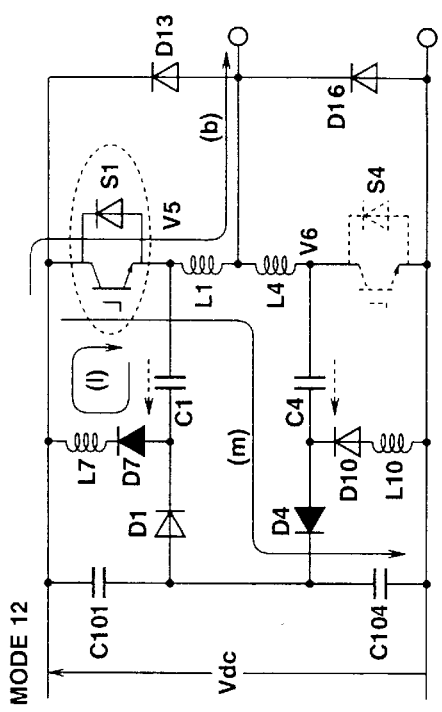
FIG.4D MODE 12
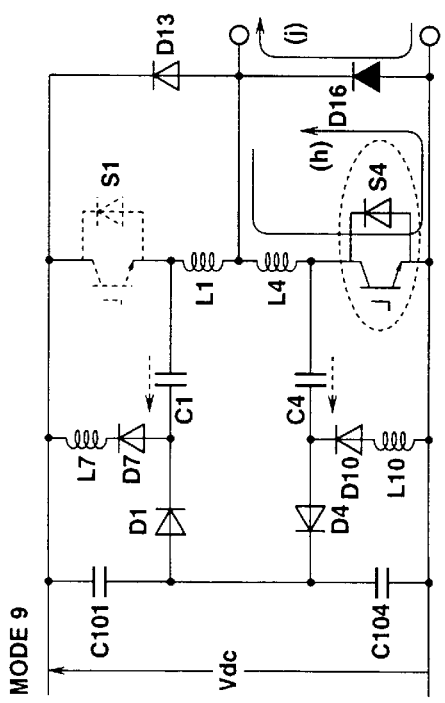
FIG.4A MODE 9
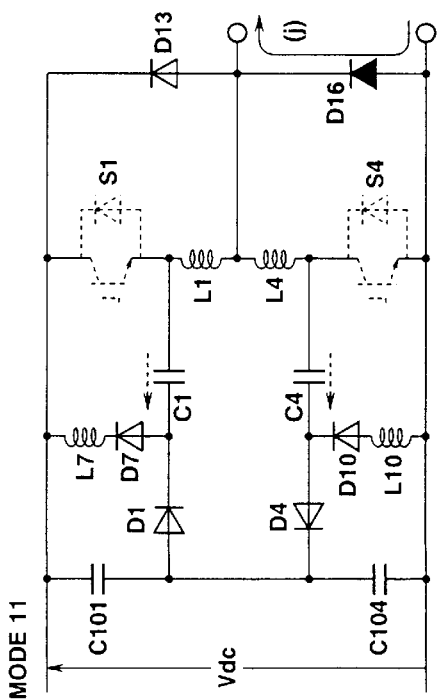
FIG.4C MODE 11

POWER CONVERTER

BACKGROUND OF THE INVENTION

The present invention relates to a power converter or power controlling system for controlling an output voltage by pulse width modulation. The power converter can be used as inverter, converter or chopper in a variable speed drive system, an uninterruptible power system (UPS) and a reactive power compensating system (SVC).

For example, a conventional inverter for driving a three phase ac motor is arranged to switch a main circuit component such as a bipolar transistor or an IGBT, and to output a PWM voltage. FIG. 12 shows one conventional example.

The three-phase inverter of FIG. 12 includes a converter section 1, an inverter main section 2 and an ac motor 3 driven by the inverter, and a control circuit 4 for controlling the inverter. The inverter main section 2 includes switching devices S1~S6. The control circuit 4 produces gate signals GS1~GS6 for the switching devices S1~S6. With these gate signals GS1~GS6, the inverter can control the average voltage by controlling the on/off duty ratio.

As main circuit element, the inverter employs bipolar transistor or IGBT in a capacity region under a few hundred KVA, and GTO beyond that region.

The high speed switching operation of a high speed switching device such as IGBT causes the output voltage to vary at high speeds. As a result, a high frequency component in the output voltage waveform is delivered as noise, and causes malfunction and failure in associated devices by radiation of radio waves, undesired magnetic coupling, or superimposition on a power line.

Therefore, a conventional inverter as shown in FIG. 13 employs one or more noise filters composed of passive components such as LCR, at input or output terminals or in control signal lines to reduce leakage of the high frequency component to the outside.

SUMMARY OF THE INVENTION

It is an object of the present invention to provide a power converting system freed from sharp changes in the output voltage and resulting noises.

The insertion of noise filters on the input and output sides to reduce the high frequency component increases the size and cost of the system. The lowering of the switching speed of IGBT to reduce the high frequency component increases switching loss in IGBT, so that the capacity of the system is limited by thermal restriction.

According to the present invention, by contrast, a pulse width modulation type power converter comprises:

positive and negative source terminals for connection with a dc power source;
a load terminal for connection to a load;
a series combination of first and second switching devices connected between the positive and negative source terminals, for alternately turning on and thereby controlling an average output voltage supplied to the load from the load terminal between the first and second switching devices by pulse width control;
a series combination of third and fourth capacitors connected between the positive and negative source terminals;
a first inductor connected in series with the first switching to form a first switching branch of the first switching device and the first inductor between the positive source terminal and the load terminal;
a second inductor connected in series with the second switching device to form a second switching branch of the second inductor and the second switching device between the load terminal and the negative source terminal;
a series combination of first diode and first capacitor connected between a first junction point between the third and fourth capacitors and a second junction point between the first switching device and the first inductor;
a series combination of second capacitor and second diode connected between a third junction point between the second inductor and the second switching device and a fourth junction point between the third and fourth capacitors;
a series combination of third diode and third inductor connected between a fifth junction point between the first diode and the first capacitor, and the positive source terminal; and
a series combination of fourth inductor and fourth diode connected between the negative source terminal and a sixth junction point between the second capacitor and the second diode.

The thus-constructed converter may be one of parallel connected circuits sections of a polyphase ac power converter.

BRIEF DESCRIPTION OF THE DRAWINGS

FIGS. 2A~2D, 3A~3D, 4A~4D and 5A~5D are circuit diagrams of the chopper of FIG. 1 in various operating modes.

DETAILED DESCRIPTION OF THE INVENTION

Figure 1:
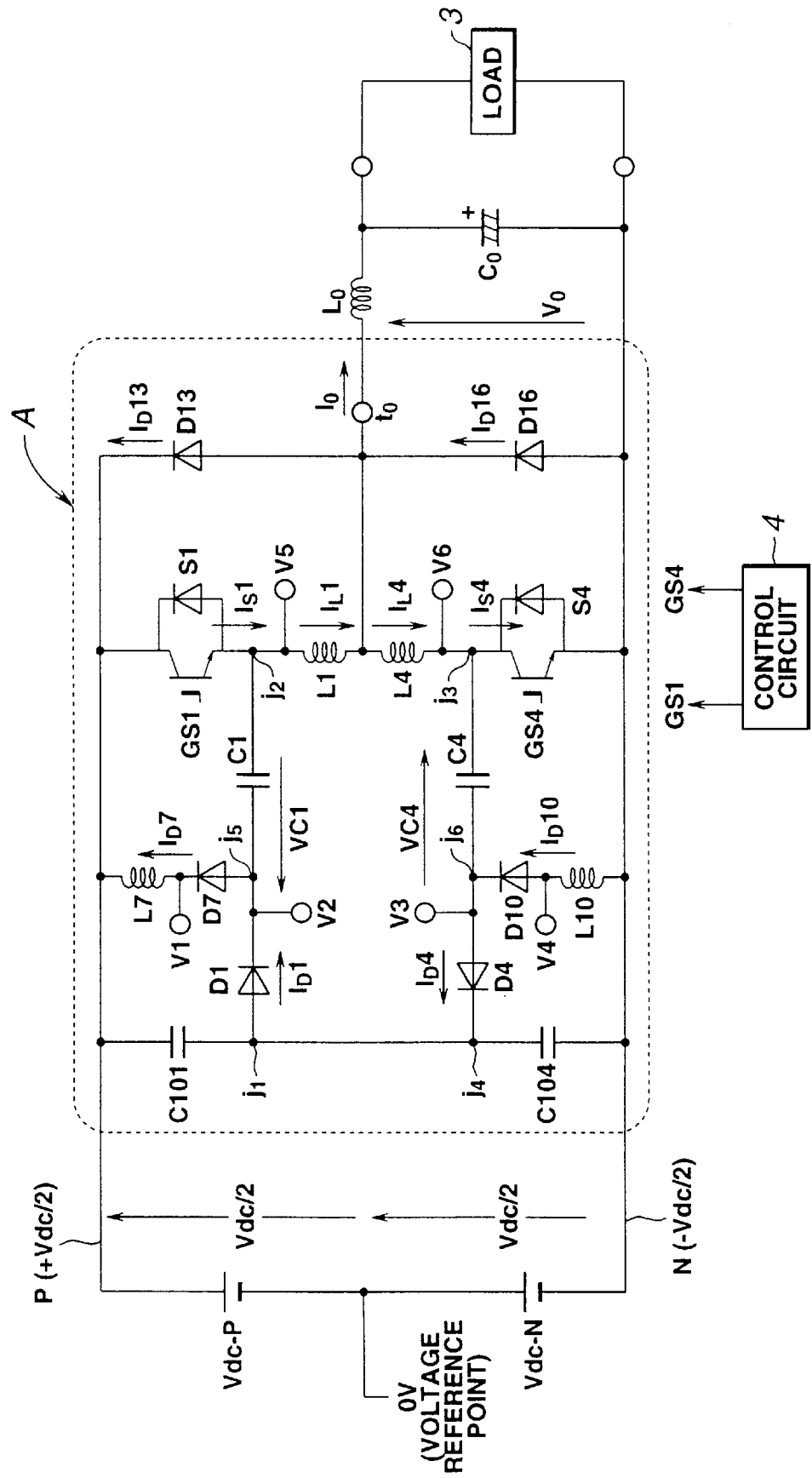
FIG. 1 is a circuit diagram showing a voltage controlling chopper in a first practical example according to the present invention.

FIG. 1 shows a voltage controlling chopper circuit in a first practical example according to a first embodiment of the present invention.

A first (or upper arm) switching device (or switch) S1, two (first and second) inductors L1 and L4 and a second (or lower arm) switching device (or switch) S2 are connected in series between positive and negative source terminals P and N for a dc source. The series combination of the inductors L1 and L4 are connected between the first and second switching devices S1 and S2. The first switching device S1 is connected between the positive source terminal P and the first inductor L1, and the second switching device S4 is between the negative source terminal N and the second inductor L4. Two (third and fourth) capacitors C101 and C104 are connected in series between the positive and negative source terminals P and N. Diodes D13 and D16 are connected in a manner of inverse parallel, respectively, with the series circuit of the switching device S1 and the inductor L1 and the series circuit of the inductance L4 and the switch S4. A load (output) terminal to is formed between the first and second inductors L1 and L4.

A series circuit of a first diode D1 and a first capacitor C1 is connected between a first junction point j1 between the third and fourth capacitors C101 and C104 and a second junction point j2 between the first switching device S1 and the first inductor L1. A series circuit of a third diode D7 and a third inductor L7 is connected between a junction point j5 between the diode D1 and the capacitor C1, and the positive source terminal P. A series circuit of a second capacitor C4 and a second diode D4 is connected between a third junction point j3 between the second inductor L4 and the second switching device S4 and a fourth junction point j4 between the third and fourth capacitors C101 and C104. A series circuit of an fourth inductor L10 and a fourth diode D10 is connected between the negative supply terminal P and a sixth junction point j6 between the second capacitor C4 and the second diode D4.

To facilitate explanation, FIG. 1 shows the dc power source in the form consisting of a first section Vdc-P and a second section Vdc-N, and a reference voltage point of 0 V is provided between the first and second sections. Between the output terminal to and the negative supply terminal N, there is connected a smoothing circuit of an inductor Lo and a dc capacitor Co, for smoothing an output voltage Vo. A dc output is supplied from the terminals of the capacitor Co, to a load 3.

The first diode D1 has a cathode connected to the fifth junction point j5 and an anode connected to the first junction point j1. The second diode D4 has a cathode connected to the fourth junction point j4, and an anode connected to the sixth junction point j6. The third diode D7 has an anode connected to the fifth junction point j5, and a cathode connected to the third inductor L7. The fourth diode D10 has a cathode connected to the sixth junction point j5, and an anode connected to the fourth inductor L10. The diode D13 has a cathode connected to the positive source terminal P and an anode connected to the load terminal to. The diode D16 has a cathode connected with the load terminal to and an anode connected to the negative source terminal N. The first switching device S1 has a first terminal connected with the positive source terminal P, a second terminal connected with the second junction point j2, and a third terminal (or control terminal) (such as a gate terminal or a base terminal) for receiving a control signal from the control circuit 4. Similarly, the second switching device S4 has a first terminal connected with the third junction point j3, a second terminal connected with the negative source terminal N, and a third terminal (or control terminal) (such as a gate terminal or a base terminal) for receiving a control signal from the control circuit 4.

In a main circuit section A of this chopper circuit, the inductors, capacitors and diodes are added to the conventional series combination of the first and second switching devices S1 and S4.

In the present invention, the main circuit section A shown in FIG. 1 is a basic circuit serving as an arm.

The circuit of FIG. 1 is operated as follows. In the following discussion, the following assumptions are made: i) power running load condition, ii) the load in the form of LR load, iii) steady state condition a while after a start of operation, iv) circuit components are ideal.

The circuit of FIG. 1 is used as a model. Current is positive in the direction shown by arrows in FIG. 1. FIG. 1 further shows potentials V1~V6 at six different points, and a neutral point in the dc power source, as a voltage reference point for providing a reference potential. The polarity of the charged voltage of each capacitor C1 or C4 is positive in the direction shown by an arrow in FIG. 1.

Figure 6:
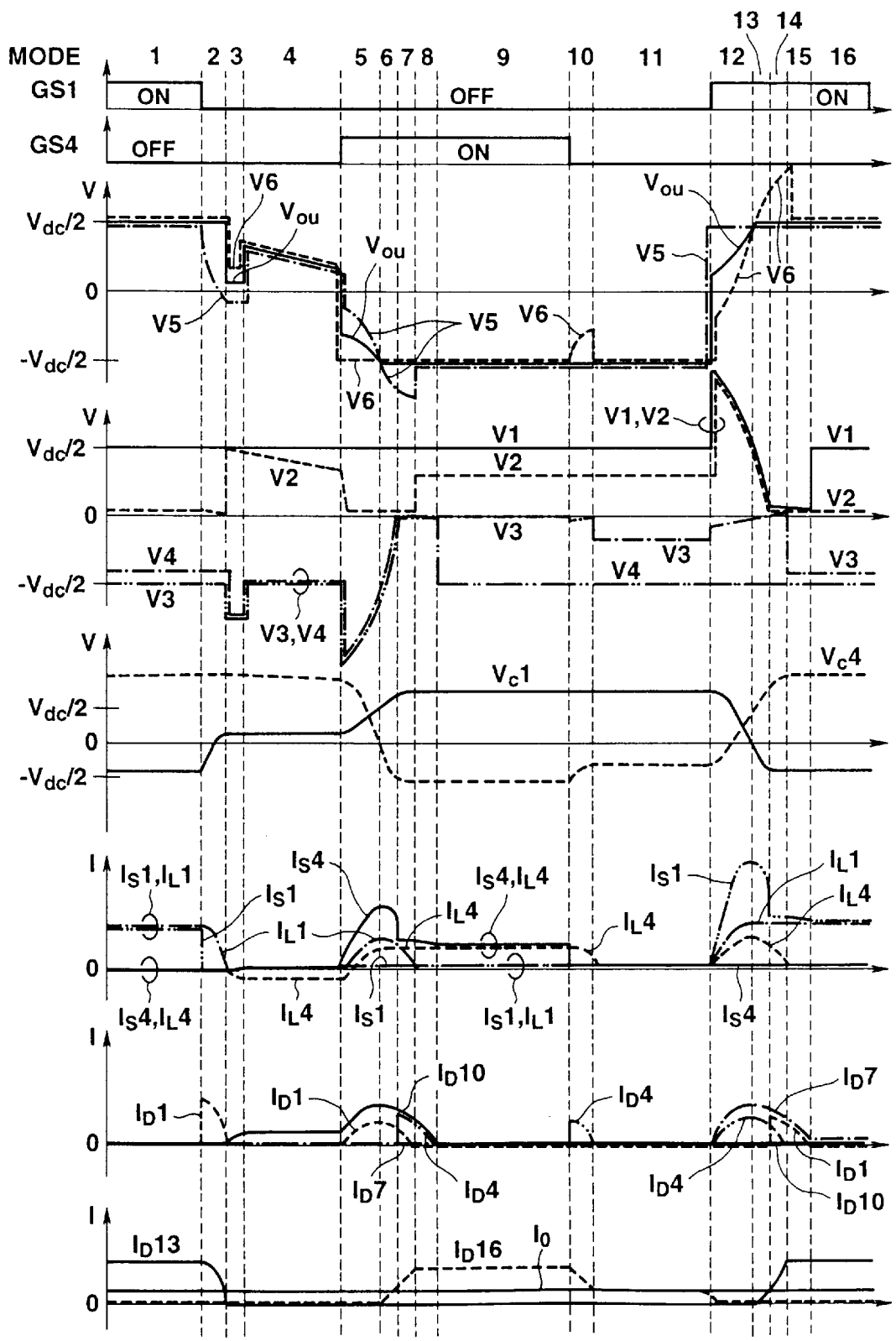
FIG. 6 is a timing chart showing currents and voltages appearing in the chopper of FIG. 1 during an operating cycle.

Under these conditions, one cycle of the PWM is divided into about 15 modes as shown in a voltage and current timing chart of FIG. 6.

FIGS. 2A~5D show current loops in each mode. In these figures, arrows of solid lines indicate current paths, and arrows of broken lines indicate the direction and approximate magnitude of a charged voltage for each of the capacitors C1 and C4. Table 1 shows the relation between PWM commands and the operating modes. FIG. 6 shows the sequence of the operating modes in the form of a time chart.

TABLE 1

| S1 | S4 | MODES | PERIODS |
|----|----|----|----|
| ON | OFF | 1 | Upper Arm ON |
| OFF |  | 2, 3, 4 | Short Prevention |
|  | ON | 5, 6, 7, 8, 9 | Lower Arm ON |
|  | OFF | 10, 11 | Short Prevention |
| ON |  | 12, 13, 14, 15, 16 | Upper Arm ON |

The sixteen modes appear in sequence as shown in FIG. 6. The on period of the first switch S1 continues from the beginning of the mode 12 until the end of the mode 1. The on period of the second switch S2 continues from the beginning of the mode 5 until the end of the mode 9. The modes 2, 3 and 4 compose a first short prevention period for preventing a short circuit. The modes 10 and 11 compose a second short prevention period. During each short prevention period, both of the first and second switches S1 and S4 are off.

Mode 1

In this mode, the gate signal GS1 for the first switch S1 is ON and the gate signal GS4 for the second switch S4 is OFF.

This condition is a power running load condition, and the load current Io is positive. In the circuit, two current paths are formed as shown by arrows (a) and (b) in FIG. 2A. The current path (a) is a closed path or loop of S1, L1 and D13. The current path (b) is a path for a load output, extending through S1 and L1 to the load.

The current path (a) is free from loss, and a constant current continues to flow. The load current Io is held approximately constant during the mode 1 since the condition is such that the inductance of the load is great. In the initial state, the charged voltage Vc1 of the capacitor C1 is of the negative polarity, and the voltage Vc4 of the capacitor C4 is positive.

Mode 2

Figure 2A:
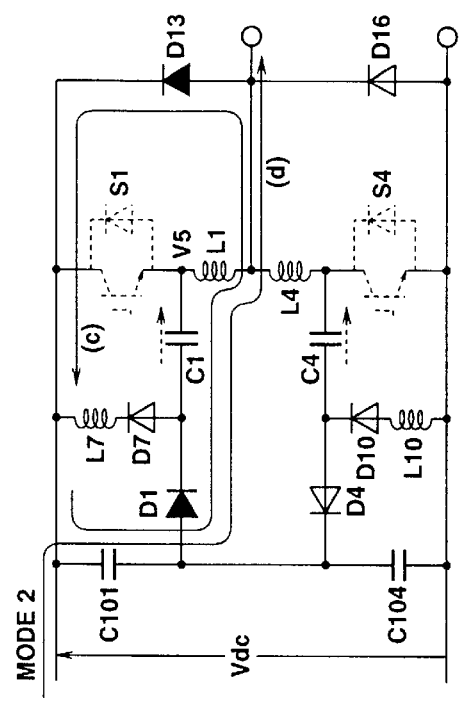
Figure 2B:
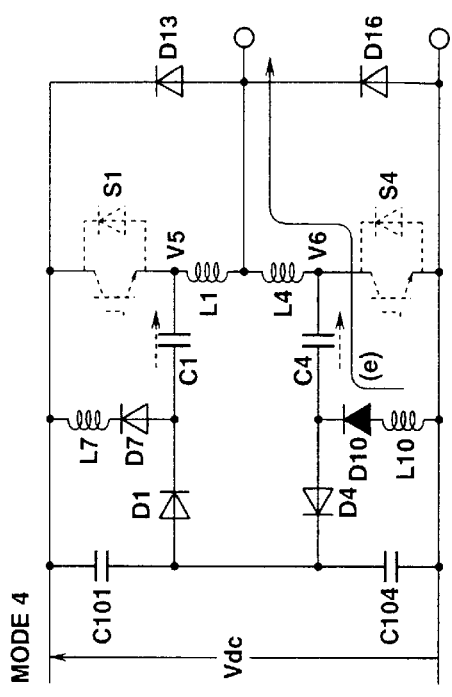

The mode 2 starts when the first gate command signal GS1 turns to the off state, and hence the first switch S1 is turned off. The inductor L1 acts to maintain the current, and produces two current paths (c) and (d), as shown in FIG. 2B. The current path (c) is a loop current path of L1, D13, C101, D1 and C1. The current path (d) is a load current path of C101, D1, C1 and L1 to the load.

By the loop current component of the path (c) and the load current Io of the path (d), the magnetic energy in L1 is converted to the charge in the capacitors C1 and C101. Therefore, the current IL through L1 decreases sharply and the voltage component Vc1 also decreases from a negative voltage.

The potential V5 on the S1 side (at j2) of the inductor L1 becomes equal to the sum of the potential at the intermediate point (j1) between C101 and C104 and the voltage Vc1 across C1. Because of energy transfer from L1, the charging to C1 acts in the direction decreasing the potential of the negative polarity, and then the charging starts in the positive direction beyond zero. In accordance with this, the potential V5 on the S1 side of L1 varies. However, the diode D13 remains conducting and hence the output voltage Vo is held constantly equal to the potential +Vdc/2 at the positive source terminal P.

Mode 3

Figure 2C:
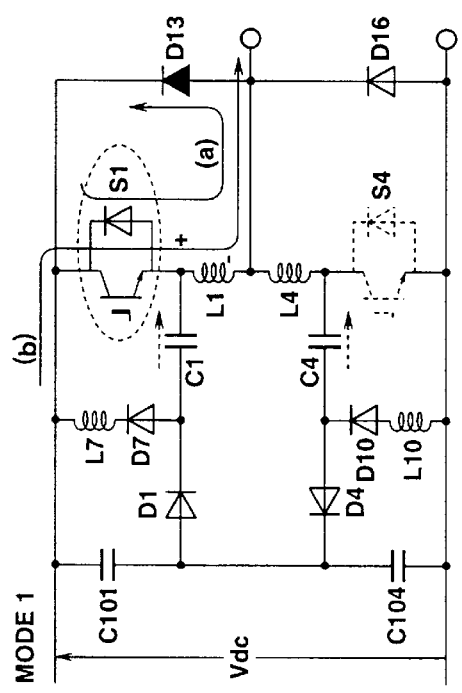
Figure 2D:
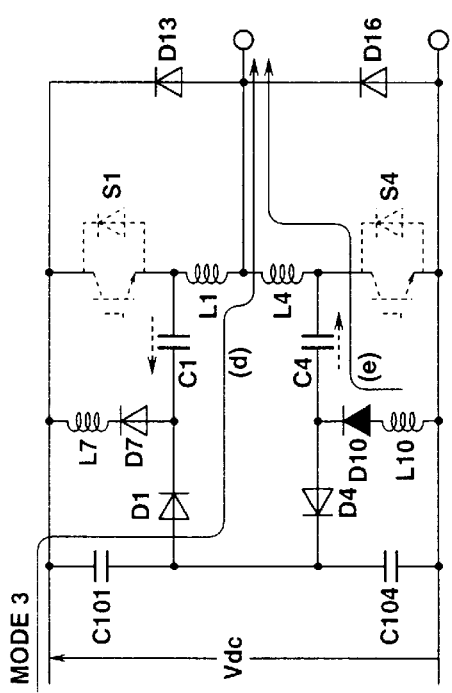

When the magnetic energy in L1 decreases, and the current $I_{L1}$ through L1 decreases below the load current, the loop current (c) flowing through the diode D13 reduces to zero. Instead, a new current path (e) is formed as shown in FIG. 2C since the current through the path (d) alone is insufficient to supply the load current. The path (e) is a current path of L10, D10, C4 and L4 to the load.

As the charged voltage Vc1 of C1 increases during the mode 3, the current is transferred or commutated from the path (d) to the path (e) until the current through the path (d) is reduced to zero at the end of the mode 3.

At that time, the potential V2 on the D7's side of C1 (at j5) becomes equal to the difference resulting from subtraction of the voltage across C101 from the potential +Vdc/2 at the positive source terminal P. The potential V5 on the S1's side of L1 is equal to the difference resulting from subtraction of the voltage Vc1 across C1 from the potential V2. The potential V6 on the S4 side of L4 sharply varies from the level of the output voltage Vo immediately before the mode 3, to the potential resulting from the potential −Vdc/2 at the negative source terminal N and the potentials of L10 and C4, by the opening of the path (e). Therefore, the output voltage Vo is equal to the potential obtained by dividing the potential of V5, V6 by L1 and L4, and the output voltage Vo varies in the same manner as V6 at the beginning of current conduction through the path (e).

Mode 4

When the magnetic energy in L1 further decreases to zero, the current component of the path (d) constituting the load current Io is reduced to zero, and the path (e) supplies all of the load current Io. At the end of the current passage through the path (d) continuing for the short-circuit preventing period (of the modes 2~4), the diodes D1 and D7 and S1 become the high impedance state, and therefore, the potential V5 on the S1 side of L1 becomes equal to the output voltage Vo. The output voltage Vo is approximately equal to the potential V6 on the S4's side of L4 provided that a change in the load current is small. Therefore, the output potential is equal to (−Vdc/2+Vc4). During the mode 4, the voltage Vc4 across C4 is decreased by the load current, and the output voltage varies in the same manner.

Mode 5

The short-circuit preventing period terminates when the on signal is supplied to the gate GS4 of the second switching device S4. The second switch S4 turns on, and opens up three current paths (d), (f) and (g), as shown in FIG. 3A. The path (d) is a load current path of C101, D1, C1 and L1 to the load. The path (f) is a current path of C101, D1, C1, L1, L4 and S4. The path (g) is a current path of C4, S4, L10 and D10. The path (g) forms a closed loop discharging the capacitor C4.

The current components of the paths (d) and (f) flow into the capacitor C1 to increase the voltage Vc1 in the positive direction, and the magnetic energy in L1 is converted to the change in C101 and C1. Conversely, the current through the path (g) discharges the capacitor C4, and the charge is converted to the magnetic energy in L10.

The potential V5 on the S1's side of L1 is equal to the difference resulting from subtraction of the voltages of C101 and C1 from +Vdc/2. The potential V6 on the S4's side of L4 is equal to −Vdc/2 since the switch S4 is on. Therefore, the output voltage is equal to the potential obtained by dividing the potential of V5 and V6 by L1 and L4.

Mode 6

When the charged potential of C1 increases during the mode 5, and the potential V5 on the S1's side of L1 reaches the level of −Vdc/2, the current through the path (f) decreases, and instead a current loop (h) is produced to sustain the current of L4. The current path (h) is a loop of L4, S4 and D16, as shown in FIG. 3C.

This current path (h) holds D16 conducting, and the output voltage Vo is fixed at −Vdc/2. The current through the path (g) continues to flow by the magnetic energy in L10 even after the voltage across C4 is reduced to zero, and charges the capacitor C4 to the opposite polarity.

Mode 7

When the voltage across C4 becomes higher than the voltage across C104 by the charging operation of the mode 6, the current of L10 starts flowing into the capacitor C104 as well as C4, and produces a current loop (i) as shown in FIG. 3C. The path (i) is a closed path of L10, D10, D4 and C104. In the case that the capacitance C104 is greater than the capacitance C4, more current flows into the capacitor C104 than to C4.

Mode 8

When the voltage across C1 increases and the resultant potential of C101 and C1 exceeds Vdc, the current of L1 reduces to zero and the current of the paths (d) and (f)

disappears. Instead, the load current Io flows through a loop (j) as shown in FIG. 3D. The path (j) is a closed path of the load, D16 and the load.

The current of the paths (i) and (g) soon disappears when the magnetic energy of L10 is used up. At that time, the commutation from S to S4 is complete. As opposed to the mode 1, the capacitor C1 is charged to a positive voltage, and the capacitor C4 is charged to a negative voltage.

Mode 9

After the completion of the mode 8, there remain only the loop paths (h) and (j). This state continues until the next mode 10 initiating the next commutation.

Mode 10

The period from the mode 10 to the mode 15 is a period for commutation from S4 to S1.

First, the switch S4 is turned off. By the turnoff of S4, the current flowing through L4 is transferred from the path (h) to a path (k) as shown in FIG. 4B. The path (k) is a loop of L4, C4, D4, C104 and D16.

Magnetic energy of L4 is converted by the current of path (k) into the charge of C4 and C104. Therefore, the current of L4 decreases, and the voltage across C4 varies in the positive direction. During this, the output voltage Vo is fixed at −Vdc/2 because of the diode D16 held conducting by the current of the path (j)

Mode 11

The current of the path (k) disappears when the magnetic energy of L4 is reduced to zero. Only the path (j) remains, as shown in FIG. 4C. This state continues during the short-circuit preventing period of the modes 10 and 11.

Mode 12

After the elapse of the short circuit preventing period, the switch S1 turns on, the current of the path (j) is reduced to zero, and three current paths (b), (l) and (m) appear, as shown in FIG. 4D. The path (l) is a loop of C1, D7, L7 and S1. The path (m) is a current path of S1, L1, L4, C4, D4 and C104.

The path (b) carries the load current Io. The current of the path (m) charges C4 and C104. The current of the path (l) acts to form a short circuit across the capacitor C1 by D7, L7 and S1. Energy is converted from the form of charge in C1 to the magnetic energy in L1.

The turn-on of the switch S1 causes a sharp variation of the potential V5 on the Si's side of L1, to +Vdc/2. The potential V6 on the S4's side of L4 becomes equal to the resultant of −Vdc/2 and the voltages of C101 and C4. The output voltage Vo is equal to the result of voltage division of the potential difference between V5 and V6 by L1 and L4. Therefore, the output voltage Vo changes at the beginning of the mode 12 and then varies gradually in accordance with the variation of the potential of C4.

Mode 13

Figure 5A:
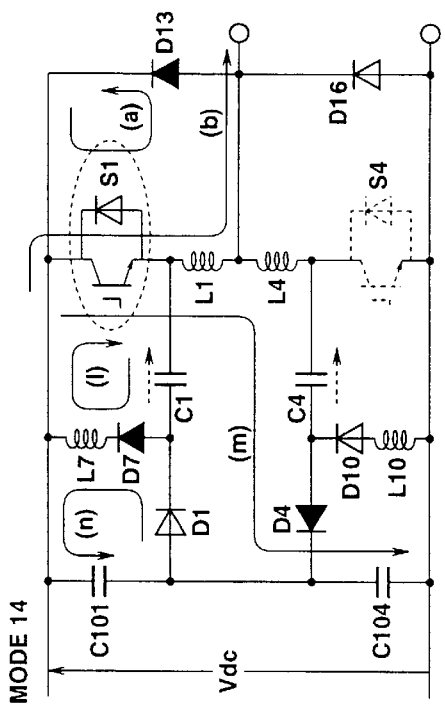

When the capacitor C4 is charged by the current through the path (m) and the resultant voltage of C104 and C4 exceeds Vdc, then the current of the path (m) starts decreasing. To sustain the current of L1, the loop current through the path (a) appears as shown in FIG. 5A, and increases as the current through the path (m) decreases. The output voltage Vo is fixed at +Vdc/2 by the diode D13 in the conducting state.

Mode 14

Figure 5B:
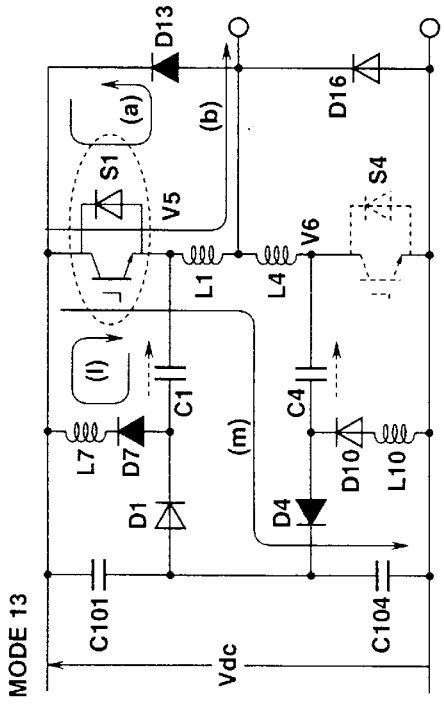

The current of L7 continues flowing even after the potential of C1 is reduced to zero by transfer of the charge of C1 to L7. Therefore, the capacitor C1 is charged to the opposite polarity. When the voltage across C1 exceeds the voltage of C101, current starts flowing into C101 through a new current path (n), as shown in FIG. 5B. The path (n) is a current path of L7, C101 and D7.

The current of L7 divides between the paths (l) and (n). When the capacitance C101 is greater than the capacitance C1, the current through the path (n) is greater than the current through the path (l). The output voltage Vo remains fixed to +Vdc/2 as in the mode 13.

Mode 15

Figure 5C:
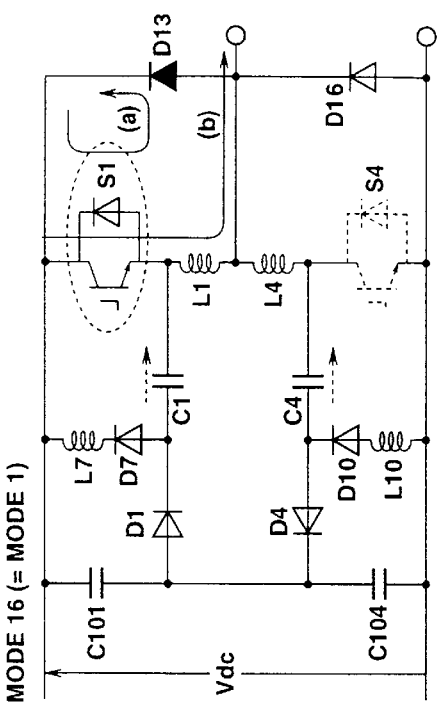

The mode 15 begins as shown in FIG. 5C when the current of L4 is reduced to zero. At that time, the capacitor C4 is charged to the maximum voltage in the positive direction and the capacitor C1 is charged to the maximum voltage in the negative direction. The output voltage Vo remains fixed to +Vdc/2 as in the modes 13 and 14.

Mode 16

Figure 5D:
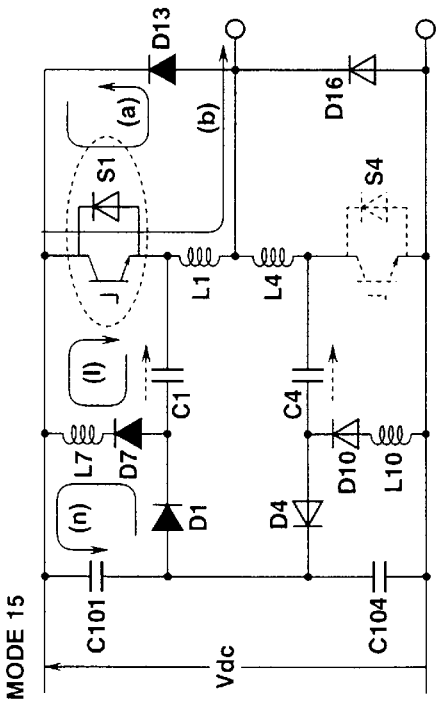

The commutation is complete when the current of L7 through the paths (n) and (l) is reduced to zero. There remain only the current components through the paths (a) and (b) as shown in FIG. 5D, and the potential at each point returns to the initial condition of the mode 1.

Within the cycle of the modes 1~16, there are four occasions at which the output voltage Vo varies at relatively high rates. They are; the starting time and ending time of the mode 3, the switching time from the mode 4 to the mode 5, and the switching time from the mode 11 to the mode 12. However, all these are caused by on/off operation of a diode. Therefore, the output voltage varies relatively gradually as compared to the conventional circuit, due to a nonlinear characteristic of a diode with respect to the magnitude of current. Thus, the circuit of FIG. 1 can prevent the output voltage from changing rapidly, and thereby reduce the noise.

Figure 7:
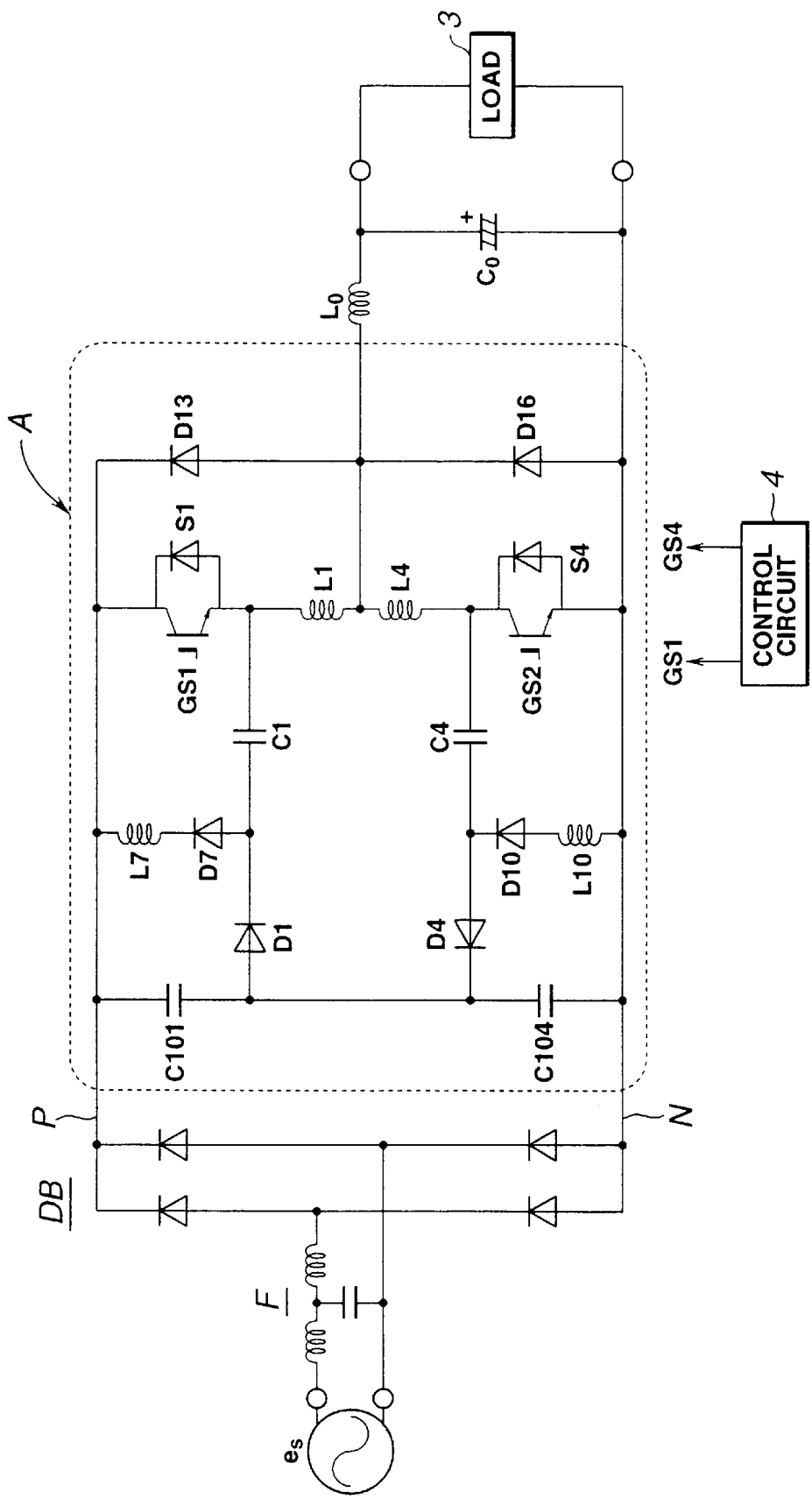
FIG. 7 is a circuit diagram of a single phase converter in a second practical example according to the present invention.

FIG. 7 shows a voltage controlling type single phase converter circuit of a second practical example according to the first embodiment of the present invention. This converter circuit employs a full-wave rectifying circuit in place of the dc power source (Vdc-p, Vdc-n) in the circuit shown in FIG. 1.

The full-wave rectifying circuit of FIG. 7 includes a single phase ac power source es, an LC filter F and a diode full-wave bridge DB. As shown in FIG. 7, a first terminal of the ac power source es is connected to a first midpoint of the bridge through two series-connected inductors, and a second terminal of the ac power source es is connected to a second midpoint. The filter F has a capacitor connected between a branch point between the two inductors connected in series with each other, and the second mid point. The diode bridge DB has four diodes connected in a bridge rectifier circuit. The first and second diodes of the bridge DB are connected in series between the positive and negative source terminals P and N, and the first midpoint is intermediate between the first and second diodes. The third and fourth diodes of the bridge DB are connected in series between the positive and negative source terminals P and N, and the second mid point is between the third and fourth diodes.

This single-phase converter can provide a source current in the form of a sine wave by detecting an input current flowing in the source and controlling the current.

Figure 8:
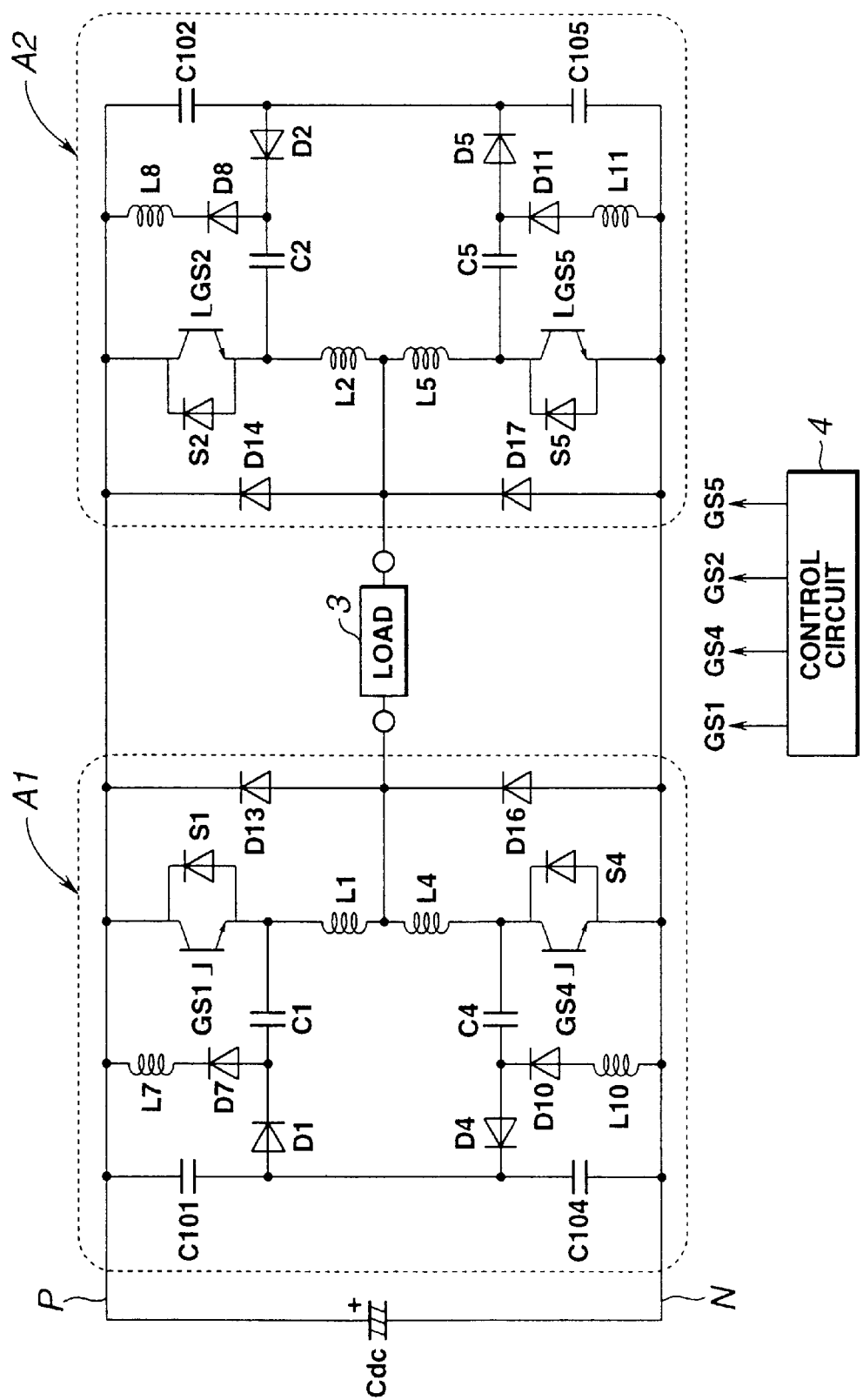
FIG. 8 is a circuit diagram of a single phase converter in a third practical example according to the present invention.

FIG. 8 shows a single-phase inverter circuit according to a third practical example of the present invention. The inverter circuit of FIG. 8 includes first and second main circuit sections (or first and second arms) A1 and A2 each of which is identical to the main circuit section A shown in FIG. 1.

The first and second circuit sections A1 and A2 are connected in parallel across a dc power source between the same positive and negative source terminals P and N. A load 3 is connected between the midpoints of the first and second circuit sections A1 and A2. The output terminal of each section A1 or A2 is connected to the load 3. A control circuit 4 controls the timings of the first and second circuit sections A1 and A2 by PWM control.

The inverter circuit of FIG. 8 constituted by the first and second circuit sections A1 and A2 having the same construction as the circuit A of FIG. 1 can reduce noise as in the first practical example.

Figure 9:
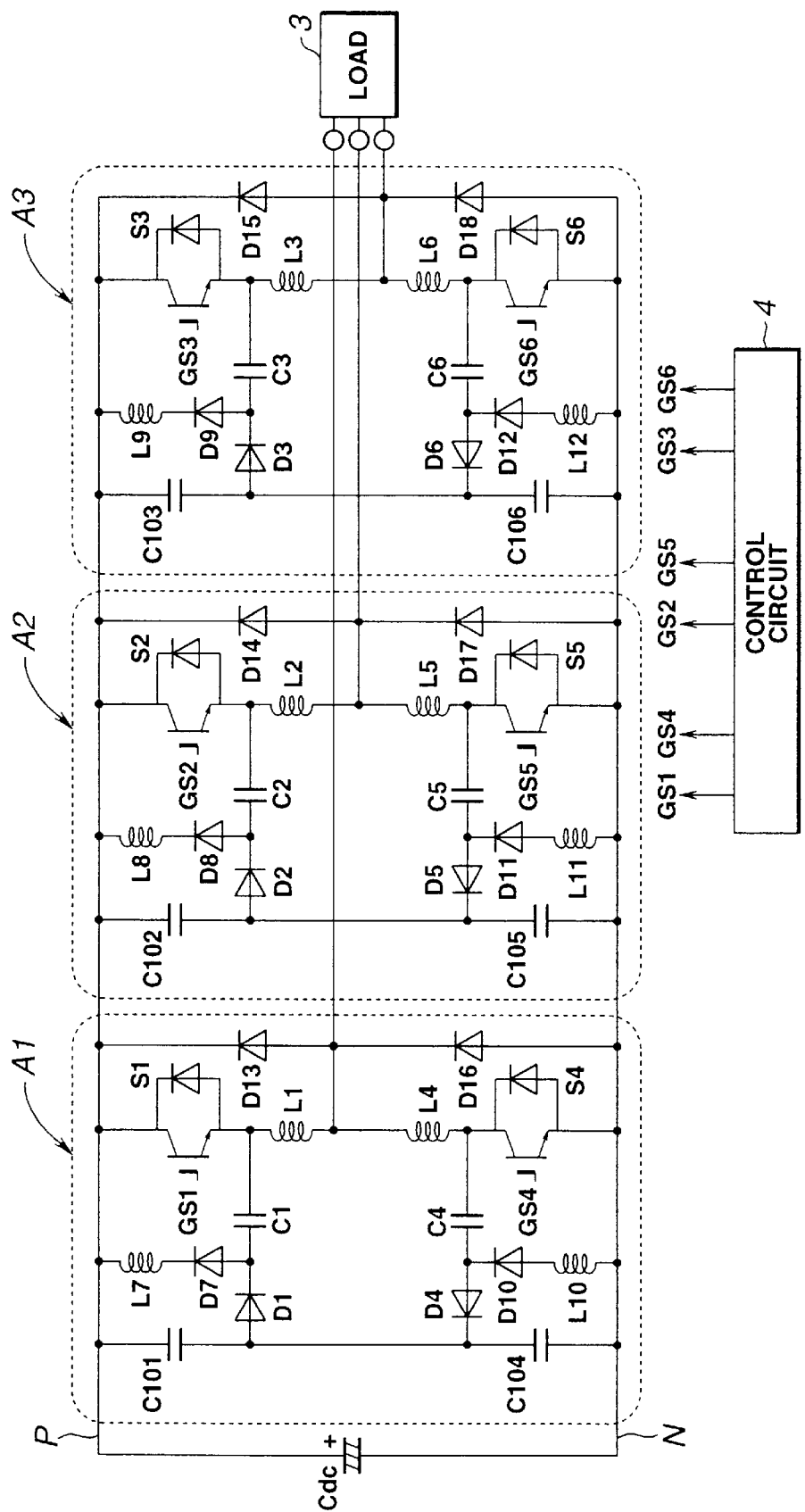
FIG. 9 is a circuit diagram of a three-phase converter in a fourth practical example according to the present invention.

FIG. 9 shows an n phase inverter circuit of a fourth practical example according to the first embodiment of the present invention. In this example, a plurality of circuit sections A1, A2, . . . each identical to the circuit A of FIG. 1 are connected in parallel between the positive and negative source terminals P and N. The number of the circuit sections A1, A2, A3 . . . is n. An n phase load 3 is connected with the midpoints of the circuit sections A1, A2, . . . A control circuit 4 controls the timings of the circuit sections A1, A2, . . . by PWM control. In the example of FIG. 9, the output terminals of the three circuit sections A1, A2 and A3 are connected, respectively, to three terminals of the three-phase load 3.

Figure 10:
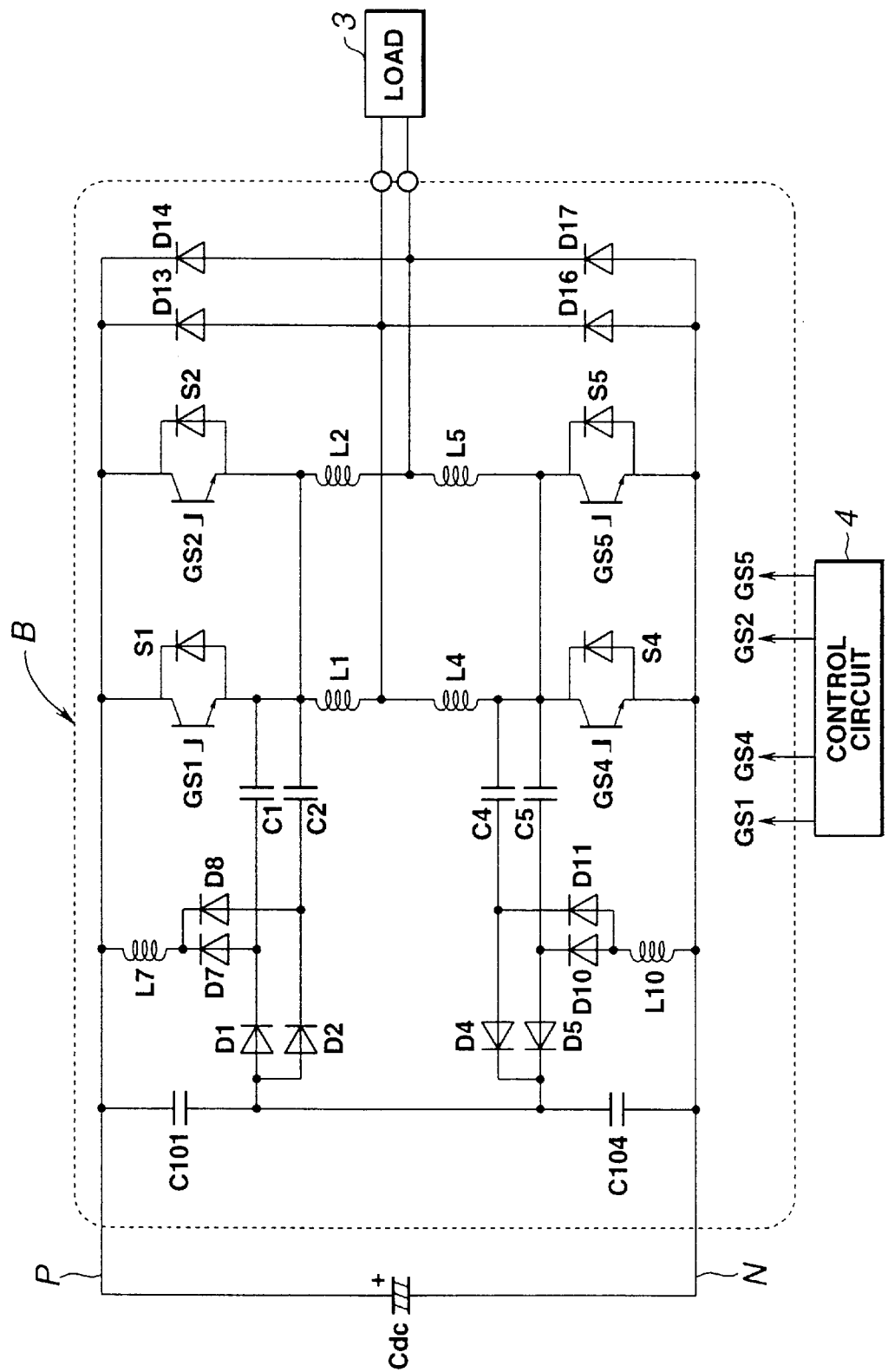
FIG. 10 is a circuit diagram of a single phase converter in a fifth practical example according to the present invention.

FIG. 10 shows a single phase inverter circuit of a fifth practical example according to the first embodiment of the present invention. A main circuit B of this inverter includes a common series branch of capacitors C101 and C104, a common reactor L7 and a common reactor L10. The common branch of the capacitors C101 and C104 of FIG. 10 serves as both of the branch of C101 and C104 in the circuit A1 of FIG. 8, and the branch of C102 and C105 in the circuit A2 of FIG. 8. The common reactor L7 of FIG. 10 serves as both of the reactors L7 and L8 of FIG. 8, and the common reactor L10 serves as both of the reactors L10 and L11 of FIG. 8. Even with these common capacitors and reactors shared by the first and second circuit sections, the inverter can function properly as evident from the timing chart of FIG. 6. It is possible to arrange the inverter circuit so that only the capacitors are shared in common, or that only the inductors are shared in common.

Figure 11:
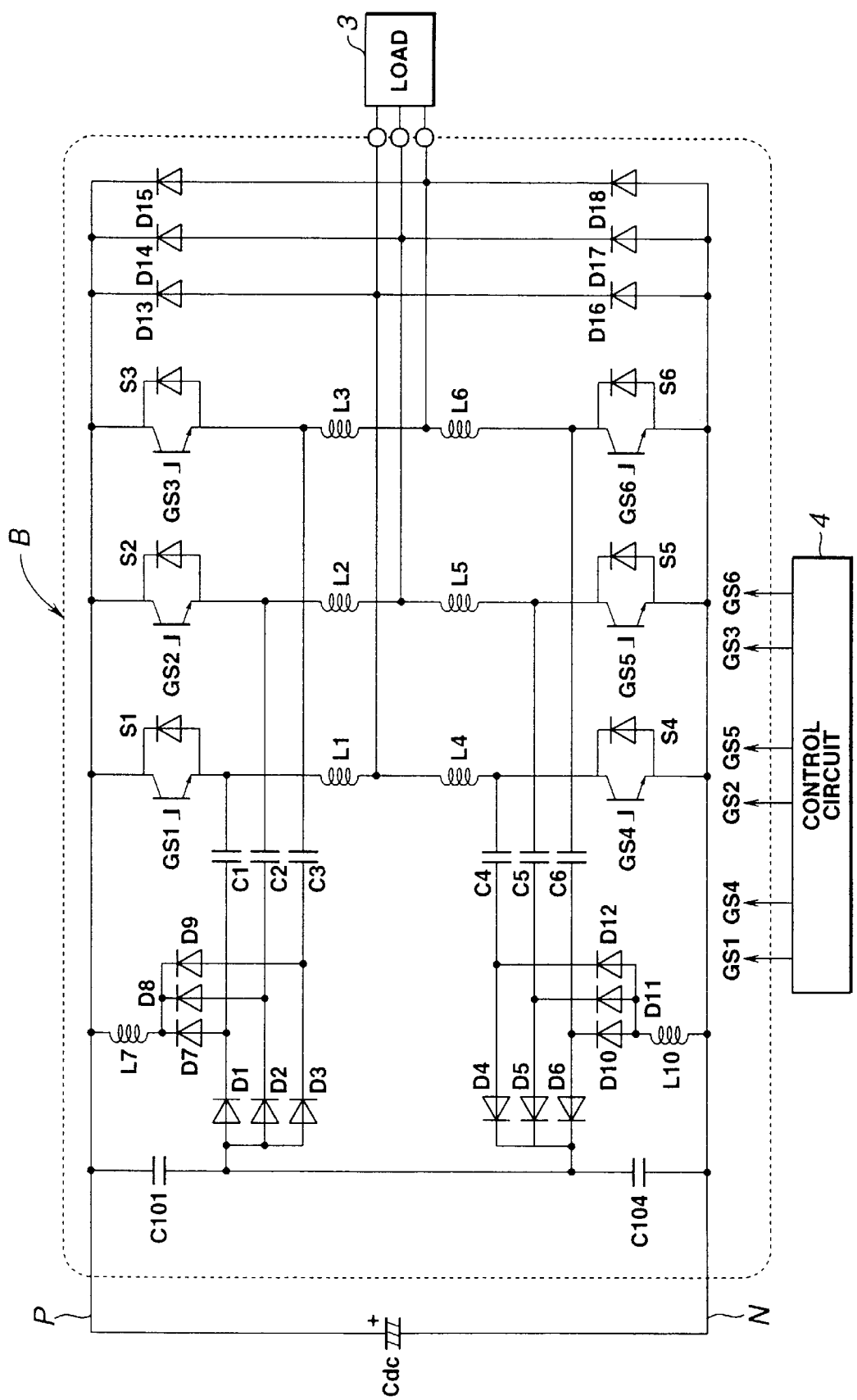
FIG. 11 is a circuit diagram of a three-phase converter in a sixth practical example according to the present invention.
Figure 12:
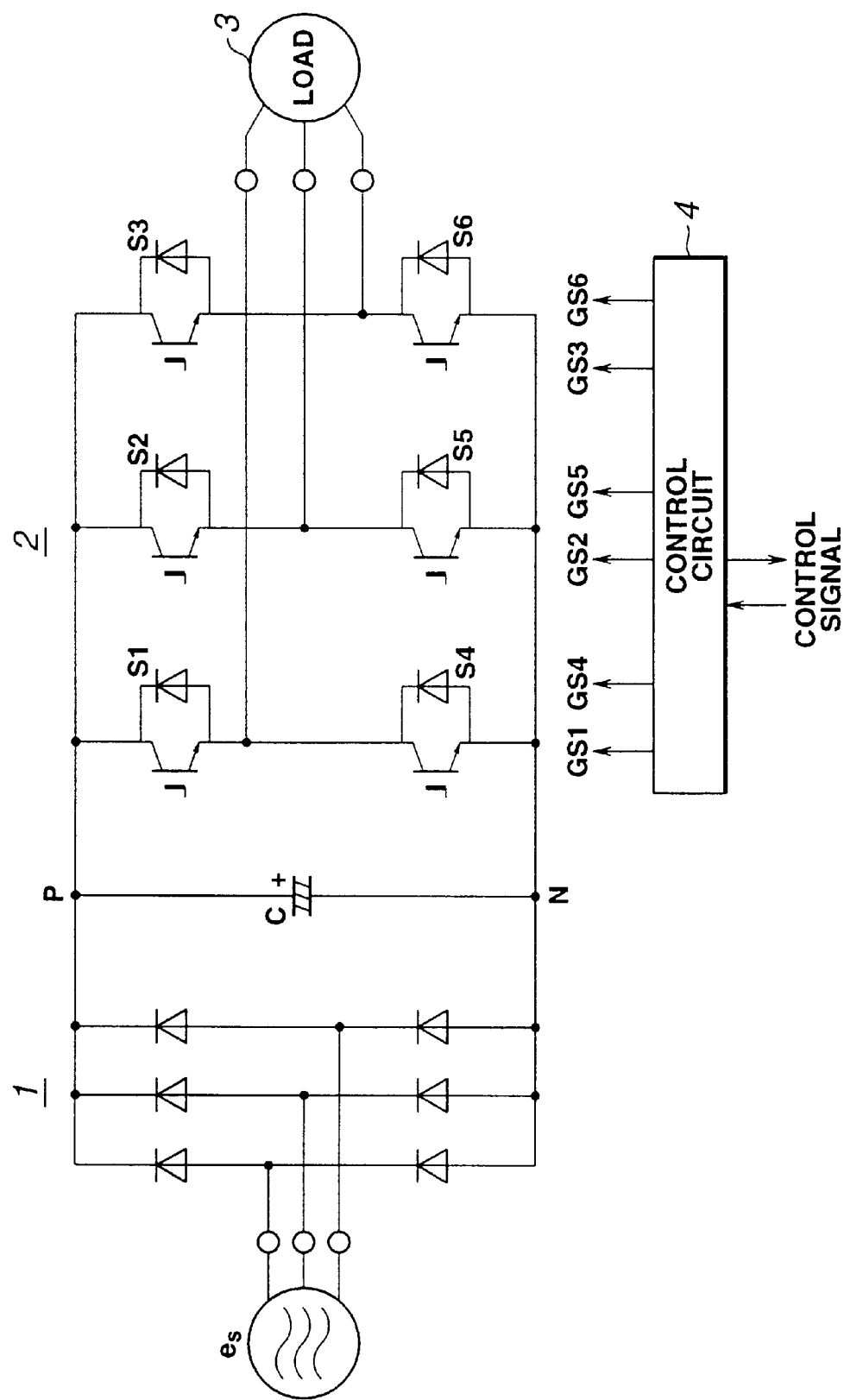
FIG. 12 is a circuit diagram of a conventional three-phase inverter.
Figure 13:
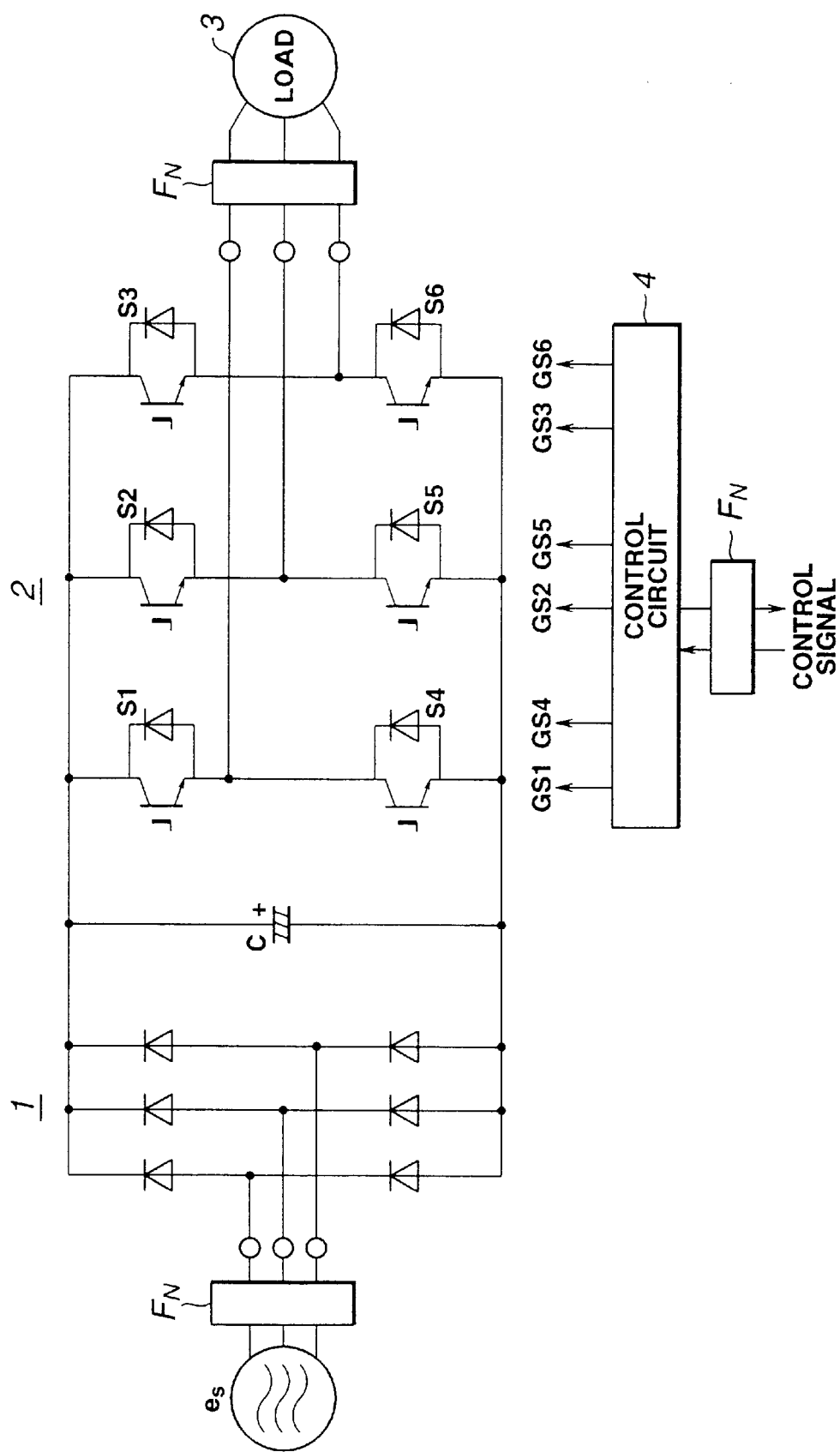
FIG. 13 is a circuit diagram of a conventional three-phase inverter with noise filters.

FIG. 11 shows a three phase inverter circuit of a sixth practical example according to the first embodiment of the present invention. In this inverter circuit, a common branch of C101 and C104 is shared by a first circuit section of S1, S4, L1, L4, D1, C1, D4, C4, D7, D10, D13 and D16, a second circuit section of S2, S5, L2, L5, D2, C2, D5, C5, D8, D11, D14 and D17, and a third circuit section of S3, S6, L3, L6, D3, C3, D6, C6, D9, D12, D15 and D18. Common reactors L7 and L10 are also shared by the first, second and third circuit sections. It is possible to arrange the inverter circuit so that only the capacitors are shared in common by the first, second and third circuit sections, or that only the inductors are shared in common by the first, second and third circuit sections.

The present invention can prevent rapid changes in the output voltage and thereby reduce noise. The present invention requires no additional switching device. The noise reduction is implemented uncostly by adding only passive devices such as inductor, capacitor and diode. In the present invention, stable control is possible only with a conventional circuit for producing PWM control signals and a circuit for setting the short-circuit preventing time. This PWM control does not require a feedback control. Therefore, the present invention is free from noise due to a sensor for the feedback control. In the circuit configuration according to the present invention, each nductance has a current circuit of a capacitor and a diode. Therefore, even if all the devices are shut off simultaneously on account of an abnormal condition such as overcurrent, the inductances do not produce surge voltage. Special protective device is not needed. In turn-off of a switching device, the current reduces to zero while the voltage of the switching device is held zero. Therefore, the present invention can reduce transient switching loss.

In the preceding examples, the circulating diodes D13 and D16 are provided to prevent the output terminal voltage from becoming excessively high during LC resonance for commutation and to limit the voltage to the level of the source voltage. At the same time, this allows the load current to recirculate during the off period of the switching devices S1 and S4. However, the addition of the diodes D13 and D16 forms a circulating loop for the resonance current in commutation, and raises the following problems.

Figure 25:
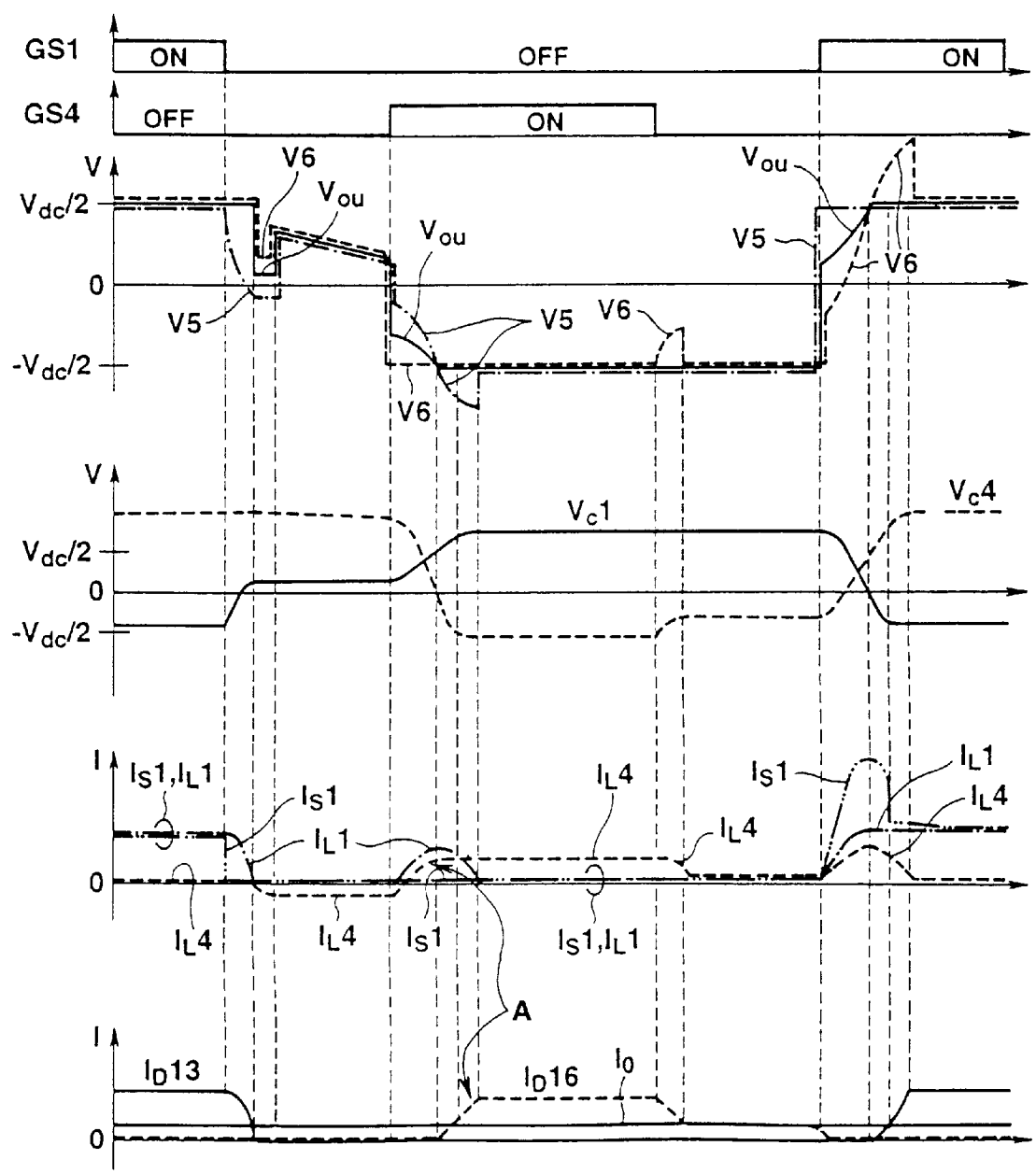
FIG. 25 is a timing chart illustrating occurrence of a circulating current in the circuit of FIG. 1.

When, in the circuit of FIG. 1, the charging current flowing through the inductor L1 into the capacitor C4 starts decreasing as shown at A in a time chart of FIG. 25, then the current of L1 reduces to zero, and the current is commutated to the diode D16. The diode D16 forms a recirculating loop with the switch S1, and the current continues flowing until the switch S1 turns off. As a result, this recirculating current increases the loss due to resistances in the switching device, the diode and the conductors, causes temperature increase by heat generation, and lowers the efficiency.

A second embodiment of the present invention is designed to avoid these problems. The second embodiment can reduce the loss due to circulating current in a noise reducing commutating circuit.

Figure 14:
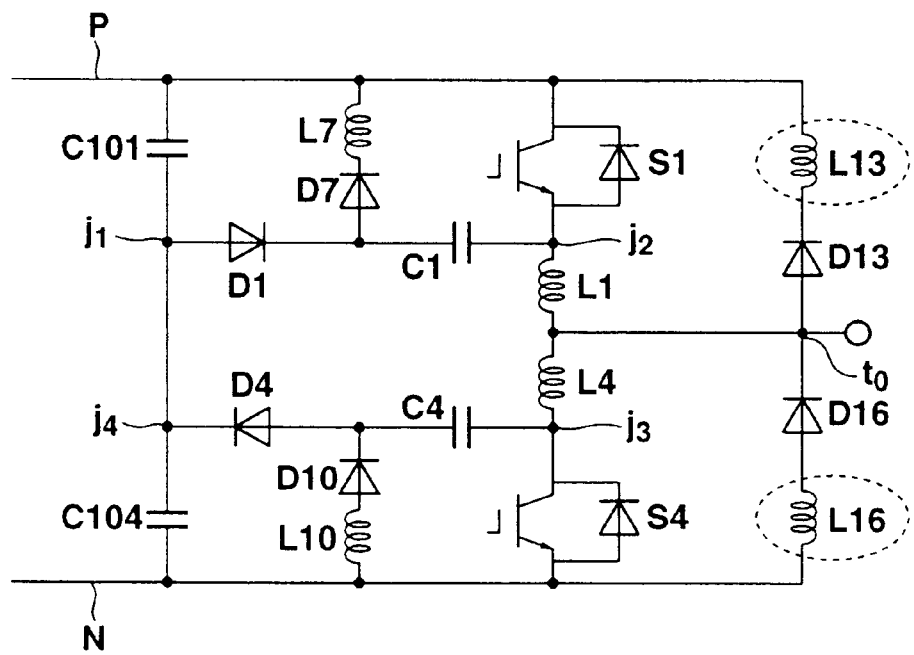
FIG. 14 is a circuit diagram of a main circuit section of a power converter in a seventh practical example according to the present invention.

FIG. 14 shows a circuit of a seventh practical example according to the second embodiment. In the circuit of FIG. 14, an inductor L13 is connected in series with the recirculating diode D13 which is in inverse parallel (or antiparallel) with the series circuit of the switching device S1 and the inductor L1. An inductor L16 is connected in series with the recirculating diode D16 which is in inverse parallel with the series circuit of the inductor L4 and the switching device S4. The inductor L13 is between the positive source terminal P and the cathode of the diode D13. The inductor 16 is between the anode of the diode D16 and the negative source terminal N.

In the portion shown at A in FIG. 25, the inductor L16 restrains an increase of the commutation current commutating to the diode D16. Similarly, the inductor L13 restrains an increase of the commutation current commutating to the diode D13.

The circuit of seventh practical example can reduce the recirculating current of the diodes D13 and D16 significantly.

Figure 15:
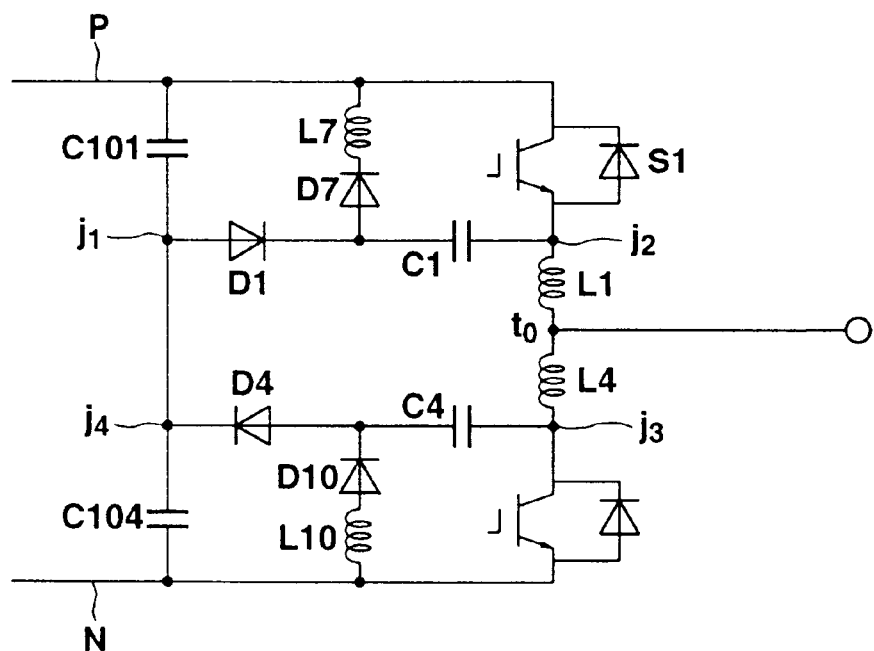
FIG. 15 is a circuit diagram of a main circuit section of a power converter in an eighth practical example according to the present invention.

FIG. 15 shows a circuit of an eighth practical example according to the second embodiment. In the eighth example, the diodes D13 and D16 are eliminated.

In the first example of FIG. 1, the magnetic energy of the inductors L1 and L4 is commutated to the diodes D13 and D16 and held as commutation current. In the circuit of FIG. 15 lacking the diodes D13 and D16, by contrast, the energy is turned into charge in the capacitors C1 and C4.

Therefore, the voltages across the capacitors C1 and C4 becomes higher. The circuit of FIG. 15 is suitable when the capacitors and devices have relatively higher voltage withstanding ability.

Figure 16:
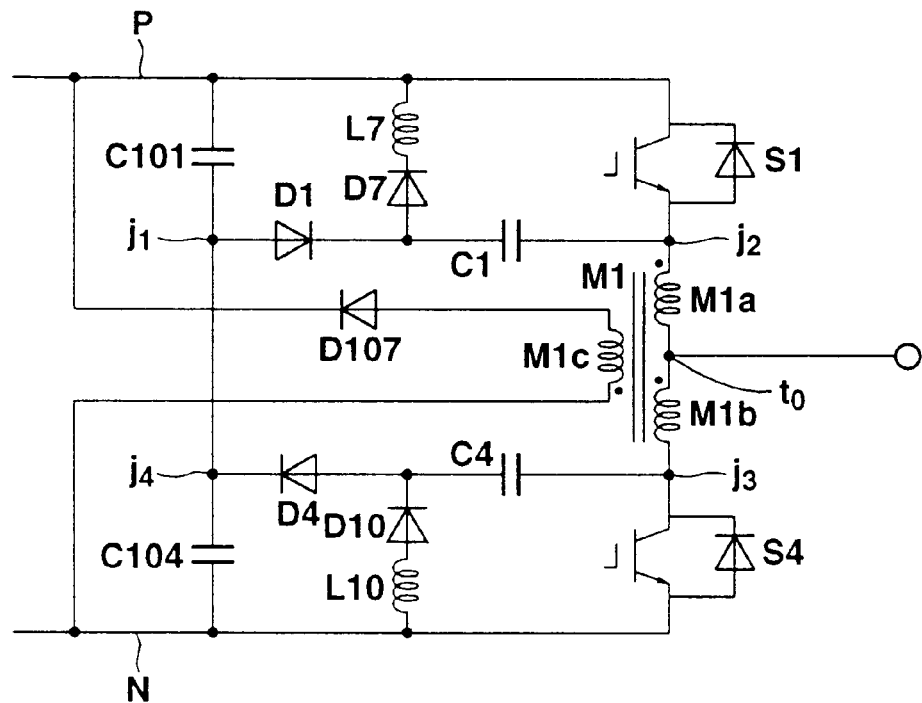
FIG. 16 is a circuit diagram of a main circuit section of a power converter in a ninth practical example according to the present invention.

FIG. 16 shows a circuit of a ninth practical example according to the second embodiment of the present invention. The ninth example does not include the recirculating diodes D13 and D16 as in the eighth example of FIG. 15. Unlike the eighth example, the ninth example employs a three winding magnetic coupling inductive component M1 in place of the inductors L1 and L4. The inductive device M1 has first, second and third windings M1$a$, M1$b$ and M1$c$ interlinked in a common magnetic circuit. The inductors L1 and L4 are replaced by the first and second windings M1$a$ and M1$b$ of the three winding magnetic coupling inductive device M1. The third winding M1$c$ is connected with the dc power source through a diode D107. As shown in FIG. 16, the third winding M1c of the inductive device M1 has a first end connected through the diode D107 to the positive source terminal P, and a second end connected to the negative source terminal N. The number of turns of the third winding M1c is greater than that of the first winding M1a and than that of the second winding M1b. The diode D107 has a cathode connected with the positive source terminal P, and an anode connected with the first end of the third winding M1c. The first and second windings M1a and M1b are connected in series between the first and second switching devices S1 and S4, and the load terminal To is between the first and second windings M1a and M1b.

When the (combined) current through the first and second windings M1a and M1b decreases, the voltage induced in the third winding M1c has the negative polarity, and the magnetic energy in the inductive device M1 is regenerated to the source. Therefore, the circuit of the ninth example can prevent the recirculating current from being generated and restrain the charged voltage of the capacitor.

Figure 17:
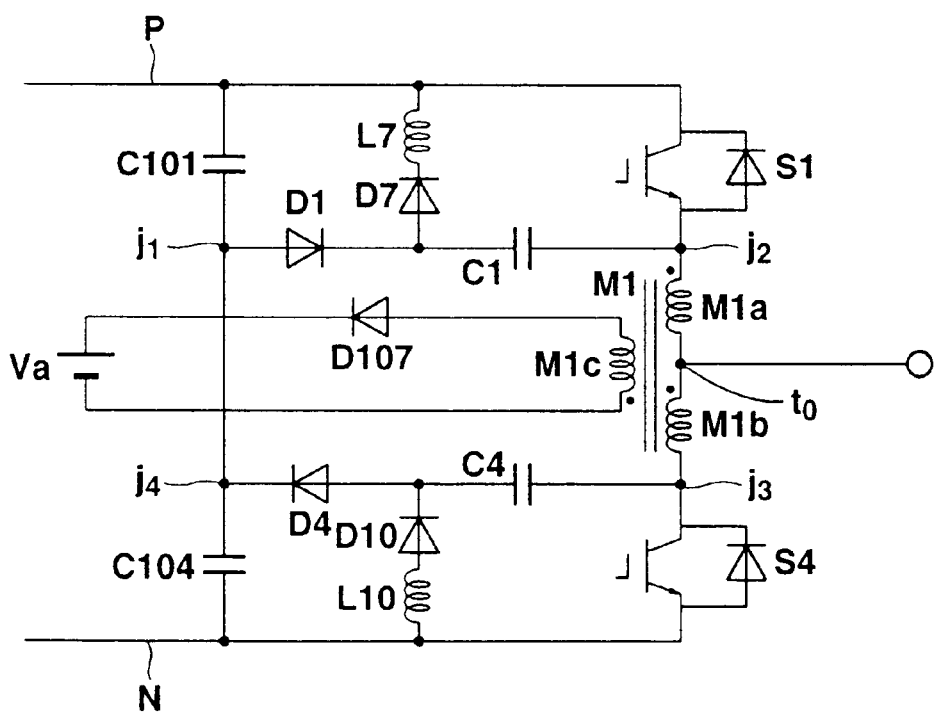
FIG. 17 is a circuit diagram of a main circuit section of a power converter in a tenth practical example according to the present invention.

FIG. 17 shows a circuit of a tenth practical example according to the second embodiment of the present invention. The third winding M1c of the three winding magnetic coupling inductive component M1 is connected with a secondary dc power source Va through a diode D107. The voltage of the secondary dc source Va is lower than the voltage of the primary dc power source connected between the positive and negative source terminals P and N. The diode D107 has a cathode connected to the positive terminal of the secondary dc source Va, and an anode connected to the first end of the third winding M1c. The second end of the third winding M1c is connected to the negative terminal of the secondary dc source Va.

In the circuit of FIG. 16, to recycle the magnetic energy of the inductive component M1 to the primary dc power source, it is required to increase the induced voltage by increasing the number of turns of the third winding M1c. Therefore, the diode D107 must endure a high reverse voltage in the situation in which the voltage is generated in the reverse direction. In the circuit of FIG. 17, by contrast, the magnetic energy in the inductive component M1 is recovered into the low voltage dc source Va. Therefore, it is not required to increase the number of turns of the third winding M1c, and it is possible to lower the withstanding voltage of the diode D107. The dc power source Va may be composed of a chopper, for example.

Figure 18:
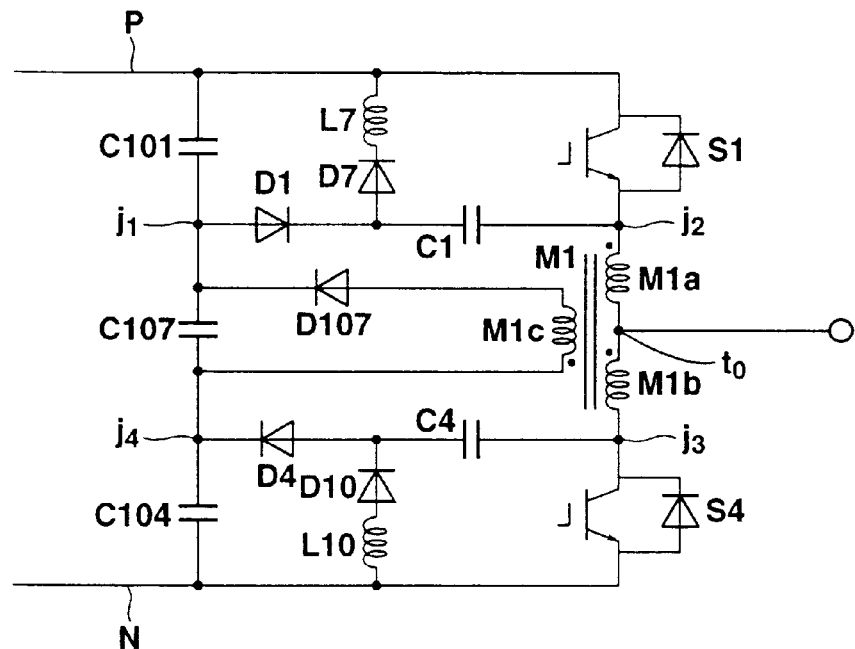
FIG. 18 is a circuit diagram of a main circuit section of a power converter in an eleventh practical example according to the present invention.

FIG. 18 shows a circuit of an eleventh practical example according to the second embodiment of the present invention. In the eleventh example, an intermediate capacitor C107 is interposed in series between the third and fourth capacitors C101 and C104. The third winding M1c of the three winding inductive component M1 is connected with the intermediate capacitor C107 through a diode D107. The intermediate capacitor C107 is between the first junction point j1 and the fourth junction point j4. The diode D107 has a cathode connected with the first junction point j1, and an anode connected with the first end of the third winding M1c. The second end of the third winding 1c is connected with the fourth junction point j4.

As the magnetic energy in the inductive component M1 decreases, the intermediate capacitor C107 is charged. The charge stored in the intermediate capacitor C107 is regenerated to the dc power source through the capacitors C101 and C104. Moreover, the charge in the intermediate capacitor C107 is transferred to the capacitor C1 through the diode D1, and to the capacitor C4 through the diode D4. The energy stored in the intermediate capacitor C107 can be regenerated to the dc power source or recycled for commutation.

Figure 19:
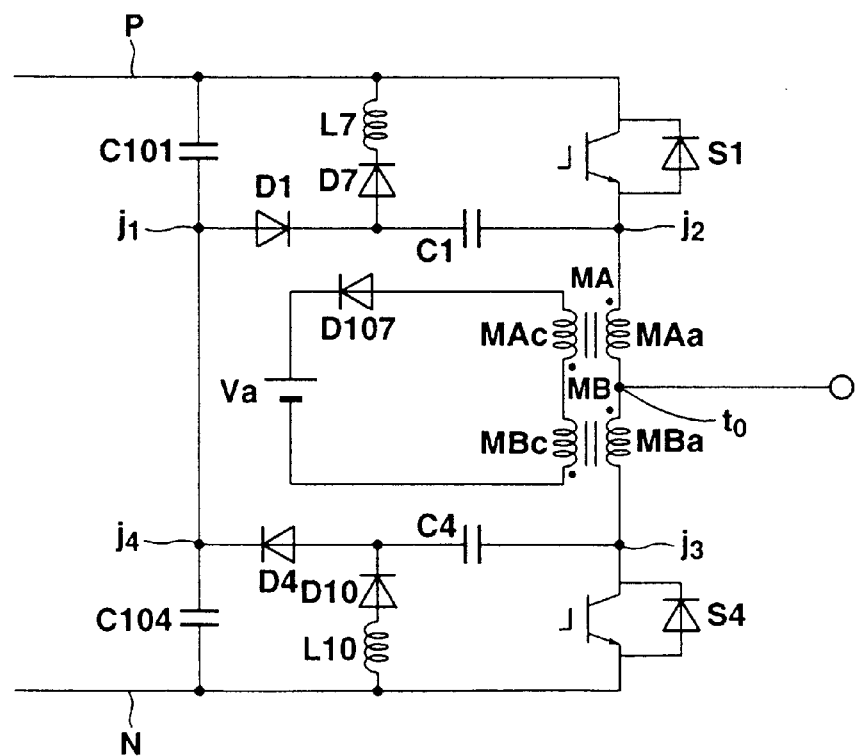
FIG. 19 is a circuit diagram of a main circuit section of a power converter in a twelfth practical example according to the present invention.

FIG. 19 shows a circuit of a twelfth practical example according to the second embodiment of the present invention. The twelfth example employs first and second two winding magnetic coupling inductive components MA and MB in place of the three winding inductive component M1. The first inductive component MA has first and second windings MAa and MAc inductively coupled together. Similarly, the second inductive component MB has first and second windings MBa and MBc. The first windings MAa and MBa of the first and second inductive components MA and MB are connected in series between the first and second switching devices S1 and S4. The second windings MAc and MBc are connected in series with the low voltage source Va through a diode D107. The load terminal To is located between the first windings MAa and MBa. The second windings MAc and MBc are connected in series. The diode D107 has a cathode connected with the positive terminal of the low voltage source Va, and an anode connected with a first end of the series combination of the second winding MAc and MBc. A second end of the series combination of MAc and MBc is connected with the negative terminal of the low voltage source Va.

The two separate inductive components MA and MB are easy to produce and assemble as compared with the three winding magnetic coupling inductive component M1, specifically when the current level is high and windings are thick.

Figure 20:
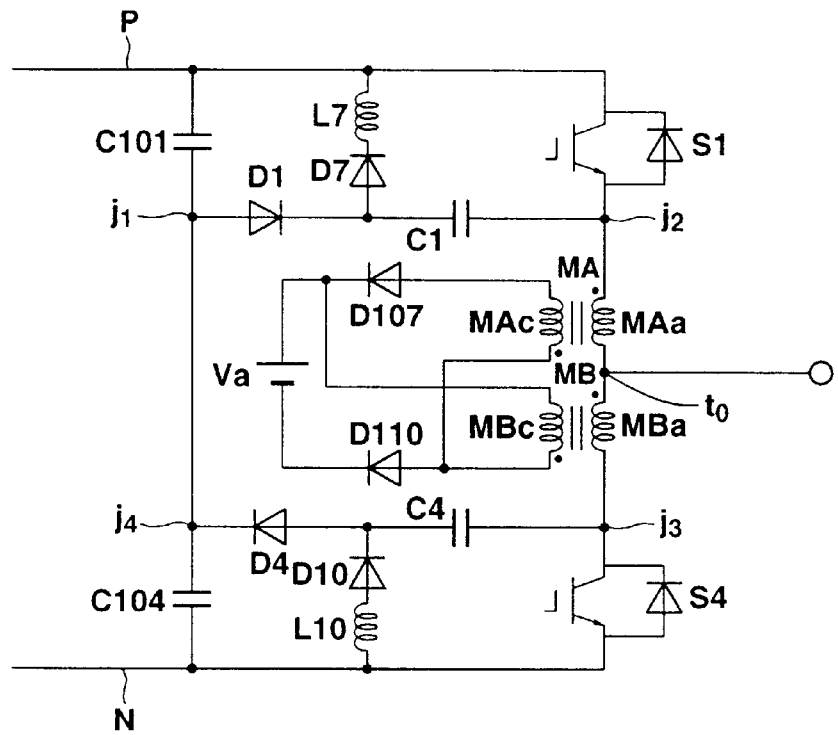
FIG. 20 is a circuit diagram of a main circuit section of a power converter in a thirteenth practical example according to the present invention.

FIG. 20 shows a thirteenth practical example. In the acircuit of FIG. 20, the second windings MAc and MBc of the first and second two winding inductive devices MA and MB are connected in parallel, respectively, through diodes D107 and D110, between the positive and negative terminals of the low voltage power source Va. The diode D107 has a cathodes connected with the positive terminal of the source Va, and an anode connected with a first end of the second winding MAc. The diode D110 has a cathode connected with the negative terminal of the low voltage power source Va, and an anode connected with second ends of the second windings MAc and MBc. A first end of the second winding MBc is connected with the positive terminal of the low voltage power source Va. This circuit configuration is advantageous specifically when the voltage of the power source Va is low.

Figure 21:
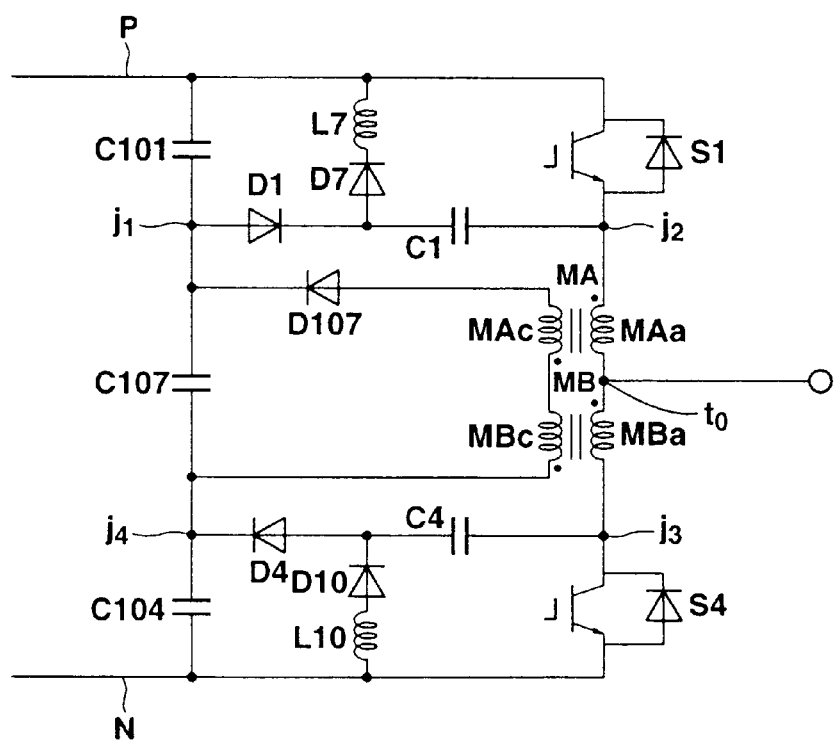
FIG. 21 is a circuit diagram of a main circuit section of a power converter in a fourteenth practical example according to the present invention.

FIG. 21 shows a fourteenth practical example. In the fourteenth example, an intermediate capacitor C107 is interposed in series between the third and fourth capacitors C101 and C104 as in the circuit of FIG. 18. The second windings MAc and MBc of the first and second two winding inductive components MA and MB are connected in series with the intermediate capacitor C107 through a diode D107. The diode D107 has a cathode connected with the first junction point j1 between C101 and C107, and an anode connected with a first end of the series combination of the windings MAc and MBc. A second end of the series combination of MAc and MBc is connected with the fourth junction point j4 between C107 and C104. Like the circuit of FIG. 18, the circuit of FIG. 21 does not require a special circuit for regenerating energy in the intermediate capacitor C107 to the power source.

Figure 22:
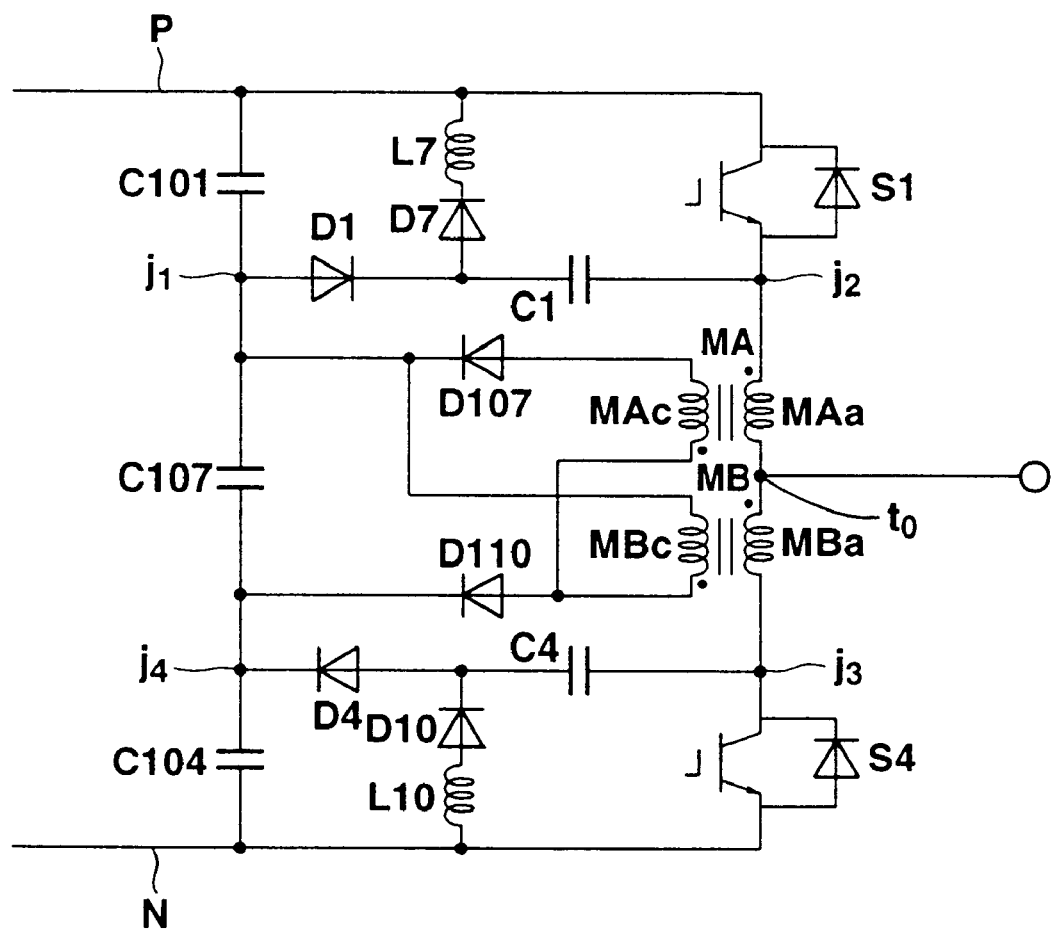
FIG. 22 is a circuit diagram of a main circuit section of a power converter in a fifteenth practical example according to the present invention.

FIG. 22 shows a fifteenth practical example. In this example, the second windings MAc and MBc of the first and second two winding inductive components MA and MB are connected in parallel, respectively, through diodes D107 and D110, with the intermediate capacitor C107 between the third and fourth capacitors C101 and C104 in the same manner as FIG. 20.

Figure 23:
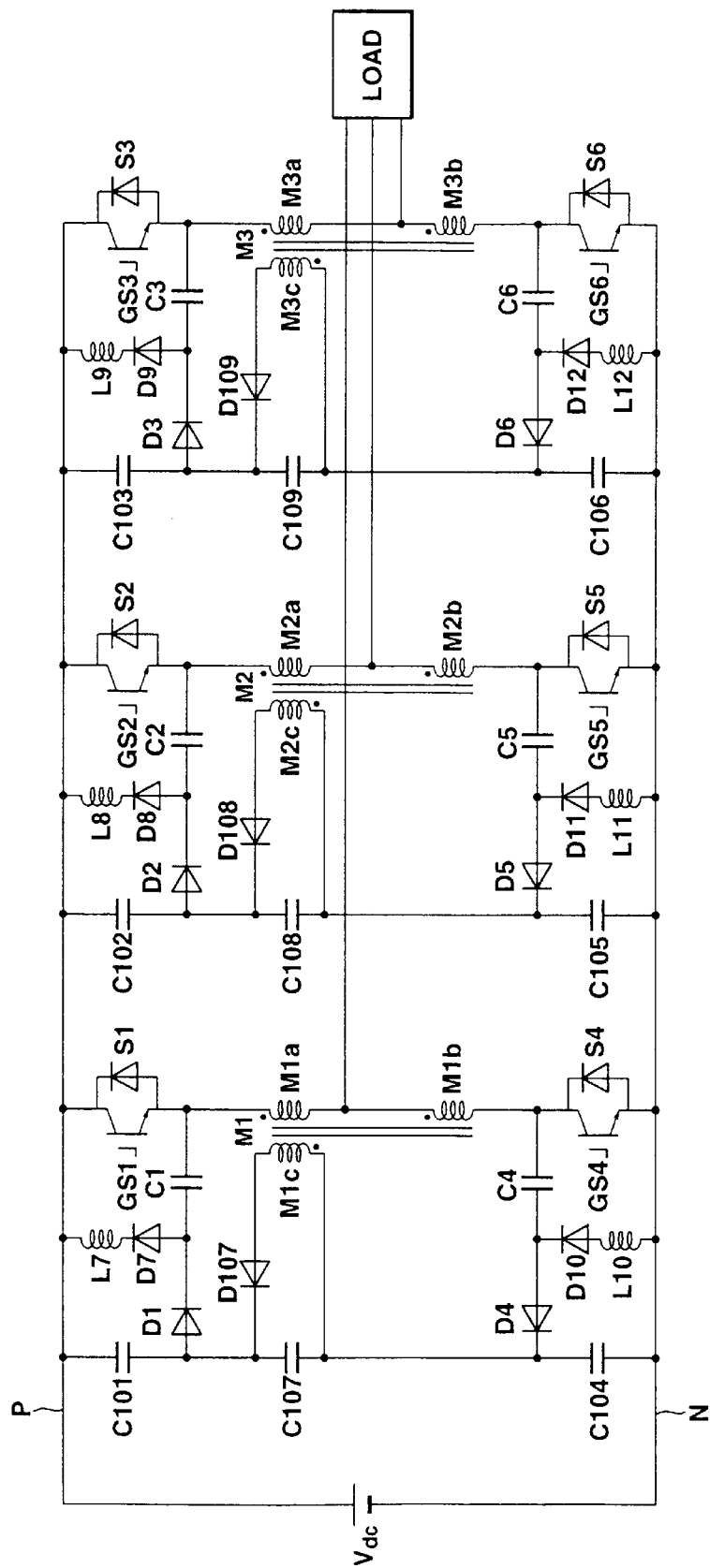
FIG. 23 is a circuit diagram of a polyphase power converter in a sixteenth practical example according to the present invention.

FIG. 23 shows a polyphase ac power converter comprising a plurality of main circuit sections each of which is substantially identical to the circuit shown in FIG. 18. Each main circuit section corresponds to one arm. The dc power source Vdc and the positive and negative source terminals P and N are common to all the main circuit sections. Energy is recycled to the common source from all the main circuit sections. In the example of FIG. 23, there are three of the main circuit sections, and the load terminals of the three main circuit sections are connected, respectively, to three terminals of the three-phase load.

Instead of the circuit configuration of FIG. 18, it is possible to employ, as each main circuit section of a polyphase ac power converter, the circuit configuration shown in any one of FIGS. 14~17 and 19~22.

Figure 24:
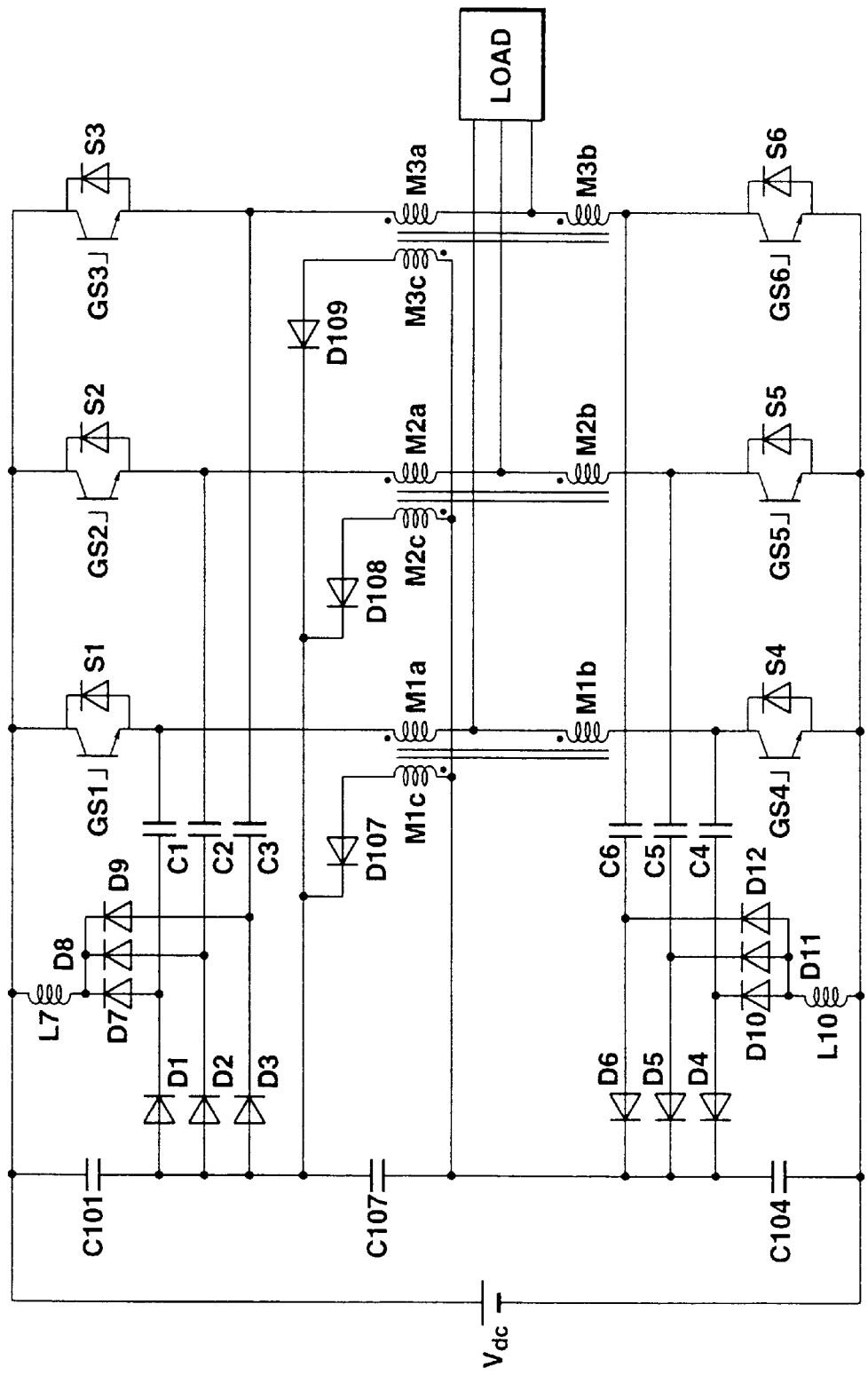
FIG. 24 is a circuit diagram of a polyphase power converter in a seventeenth practical example according to the present invention.

FIG. 24 shows a seventeenth practical example. In this example, a common branch of C101, C107 and C104, a common inductor L7 and a common inductor L10 are shared by a plurality of main circuit sections. In the example of FIG. 24, there are three of the main circuit sections. The first section includes S1, S4, M1 (M1a, M1b and M1c), D1, C1, D4, C4, D7 and D10. The second circuit section includes S2, S5, M2, D2, C2, D5, C5, D8 and D11. The third circuit section includes S3, S6, M3, D3, C3, D6, C6, D9 and D12.

It is possible to modify the circuit of FIG. 24 so that only the capacitors C101, C107 and C104 are shared in common by the main circuit sections as shown in FIG. 24, and there are provided individual inductors L7, L8, L9, L10, L11 and L12 in the manner as shown in FIG. 23. Instead of the circuit configuration of FIG. 18, it is possible to employ, as each main circuit section of the polyphase ac power converter of FIG. 24 or its variation, the circuit configuration shown in any one of FIGS. 14~17 and 19~22. In the case of FIG. 17, 19 or 20, it is possible to arrange so that the secondary dc source Va is common to all the main circuit sections.

Thus, it is possible to employ one of the circuit designs of FIGS. 14~22 as the configuration of main circuit sections, and form a polyphase system by a parallel combination of these equal main circuit sections. In the thus-constructed polyphase system, it is further possible to arrange all or part of the capacitors C101, C104 and C107, the inductors L7 and L10 and the secondary source Va as common component to the constituent main circuit sections.

The second embodiment of the present invention as illustrated in FIGS. 14~24 can reduce the loss due to recirculating current by restraining or eliminating the recirculating current which could be at peak current value of resonance current.

In the examples employing one or more inductive devices or transformers (M1, M2, M3, MA, MB) having inductively coupled windings as shown in FIGS. 16~24, magnetic energy can be readily recovered, and the energy recovery helps lower the capacitor voltages.

What is claimed is:

1. A PWM power converter comprising:
   positive and negative source terminals for connection with a dc power source;
   a load terminal for connection to a load;
   a series combination of first and second switching devices connected between the positive and negative source terminals, for alternately turning on and thereby controlling an average output voltage supplied to the load from the load terminal between the first and second switching devices by pulse width control;
   a series combination of third and fourth capacitors connected between the positive and negative source terminals;
   a first inductor connected in series with the first switching device to form a first switching branch of the first switching device and the first inductor between the positive source terminal and the load terminal;
   a second inductor connected in series with the second switching device to form a second switching branch of the second inductor and the second switching device between the load terminal and the negative source terminal;
   a series combination of first diode and first capacitor connected between a first junction point between the third and fourth capacitors and a second junction point between the first switching device and the first inductor;
   a series combination of second capacitor and second diode connected between a third junction point between the second inductor and the second switching device and a fourth junction point between the third and fourth capacitors;
   a series combination of third diode and third inductor connected between a fifth junction point between the first diode and the first capacitor, and the positive source terminal; and
   a series combination of fourth inductor and fourth diode connected between the negative source terminal and a sixth junction point between the second capacitor and the second diode.

2. The power converter according to claim 1 wherein the power converter further comprises the dc power source connected between the positive and negative source terminals, and wherein the dc power source comprises a single phase ac power source, an LC filter and a full-wave diode bridge.

3. The power converter according to claim 1 wherein the power converter further comprises a first circulating diode connected between the load terminal and the positive source terminal, and a second circulating diode connected between the negative source terminal and the load terminal.

4. The power converter according to claim 3 wherein the power converter further comprises a fifth inductor connected in series with the first circulating diode, for limiting a current through the first circulating diode, and a sixth inductor connected in series with the second circulating diode, for limiting a current through the second circulating diode.

5. The power converter according to claim 1 wherein the first inductor includes a first winding, the second inductor includes a second winding, and the first and second windings are inductively coupled.

6. The power converter according to claim 5 wherein the power converter comprises a multi-winding inductive coupling component comprising the first winding, the second winding and a third winding for energy regeneration.

7. The power converter according to claim 6 wherein the third winding is connected between the positive and negative source terminals through a fifth diode.

8. The power converter according to claim 6 wherein the third winding is connected across a lower dc voltage source through a fifth diode, and wherein the power converter comprises the dc power source connected the positive and negative source terminals and a supply voltage of the lower dc voltage source is lower than a supply voltage of the dc power source between the positive and negative source terminals.

9. The power converter according to claim 6 wherein the third winding is connected through a fifth diode across an intermediate capacitor connected between the third and fourth capacitors, the first junction point is intermediate between the third capacitor and the intermediate capacitor, and the fourth junction point is intermediate between the intermediate capacitor and the fourth capacitor.

10. The power converter according to claim 1 wherein the power converter comprises a first multi-winding inductive coupling component comprising first and second windings, a second multi-winding inductive coupling component comprising first and second windings, the first inductor is the first winding of the first multi-winding inductive coupling component, the second inductor is the first winding of the second multi-winding inductive coupling component, and each of the second windings is connected with an energy regenerating component.

11. The power converter according to claim 10 wherein the second windings of the first and second multi-winding inductive coupling components are connected in series with each other, and a series combination of the second windings of the first and second multi-winding inductive coupling component is connected through a fifth diode with the energy regenerating component.

12. The power converter according to claim 10 wherein the second windings of the first and second multi-winding inductive coupling components are connected, respectively through fifth and sixth diodes, with the energy regenerating component.

13. The power converter according to claim 10 wherein the energy regenerating component is a lower dc voltage source.

14. The power converter according to claim 10 wherein the energy regenerating component is an intermediate capacitor connected between the third and fourth capacitors, the first junction point is between the third capacitor and the intermediate capacitor, and the fourth junction point is between the intermediate capacitor and the fourth capacitor.

15. The power converter according to claim 1 wherein the power converter is a polyphase ac converter, and comprises a parallel combination of converting circuit sections each comprising the first switching branch of the first switching device and the first inductor, the second switching branch of the second inductor and the second switching device, a first capacitive branch of the first diode and the first capacitor, and a second capacitive branch of the second capacitor and the second diode.

16. The power converter according to claim 15 wherein each of the converting circuit sections further comprises the third diode and the fourth diode; and wherein the positive source terminal is a common positive source terminal common to the converting circuit sections, the negative source terminal is a common negative source terminal common to the converting circuit sections, and the load terminal is separately provided for each of the converting circuit section.

17. The power converter according to claim 16 wherein the third inductor is a positive side common inductor common to the converting circuit sections, the fourth inductor is a negative side common inductor common to the converting circuit sections, the positive side common inductor is connected between the common positive source terminal and the third diode of each converting circuit section, the negative side common inductor is connected between the common negative source terminal and the fourth diode of each converting circuit section.

18. The power converter according to claim 16 wherein the third capacitor is a positive side common capacitor, the fourth capacitor is a negative side common capacitor, the series combination of the positive and negative side common capacitors is common to the converting circuit sections, the series combination of the first diode and the first capacitor of each converting circuit section is connected between the first junction point between the positive and negative side common capacitors and the second junction point between the first switching device and the first inductor of each converting circuit section, and the series combination of the second capacitor and the second diode of each converting circuit section is connected between the third junction point between the second inductor and the second switching device of each converting circuit section and the fourth junction point between the positive and negative side common capacitors.

19. The power converter according to claim 18 wherein the first inductor of each converting circuit section comprises a first winding, the second inductor of each converting circuit section comprises a second winding, and each converting circuit section comprises a third winding inductively coupled with at least one of the first and second windings.

20. The power converter according to claim 19 wherein the third winding of each converting circuit section is connected through a fifth diode with a common regenerative circuit section common to the converting circuit sections.

21. The power converter according to claim 20 wherein the common regenerative circuit section comprises a common intermediate capacitor connected between the positive and negative side common capacitors, the first junction point of each converting circuit section is intermediate between the positive side common capacitor and the common intermediate capacitor, and the fourth junction point of each converting circuit section is intermediate between the common intermediate capacitor and the negative side common capacitor.

22. The power converter according to claim 20 wherein the common regenerative circuit section comprises a common lower dc voltage source, and a supply voltage of the lower dc voltage source is lower than a supply voltage of the dc power source between the common positive and negative source terminals.

23. The power converter according to claim 20 wherein the first, second and third windings are inductively coupled together.

24. The power converter according to claim 20 wherein the first winding is inductively coupled with the third winding, the second winding is inductively coupled with a fourth winding connected with the common regenerative circuit section.

25. The power converter according to claim 24 wherein the third and fourth windings of each converting circuit section are connected in series to form a series combination of the third and fourth windings which is connected through the fifth diode with the common regenerative circuit section.

26. The power converter according to claim 24 wherein the third and fourth windings of each converting circuit section are connected through the fifth diode and a sixth diode, respectively, with the common regenerative circuit section.

27. The power converter according to claim 1 wherein the power converter further comprises a control circuit for turning on the first and second switching devices alternately, the first inductor is connected between the first switching device and the load terminal, and the second inductor is connected between the load terminal and the second switching device.

* * * * *